United States Patent
Day et al.

(10) Patent No.: US 10,799,473 B2
(45) Date of Patent: Oct. 13, 2020

(54) METHODS OF INHIBITING IGF-1R ACTIVATION OR DOWNTREAM SIGNALLING THEREOF TO REDUCE RADIATION-INDUCED CELLULAR SENESCENCE

(71) Applicant: The Henry M. Jackson Foundation for the Advancement of Military Medicine, Inc., Bethesda, MD (US)

(72) Inventors: Regina M Day, Rockville, MD (US); Ronald-Allan M Panganiban, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 669 days.

(21) Appl. No.: 14/771,171

(22) PCT Filed: Mar. 3, 2014

(86) PCT No.: PCT/US2014/020042
§ 371 (c)(1),
(2) Date: Aug. 27, 2015

(87) PCT Pub. No.: WO2014/137946
PCT Pub. Date: Sep. 12, 2014

(65) Prior Publication Data
US 2016/0000744 A1 Jan. 7, 2016

Related U.S. Application Data

(60) Provisional application No. 61/772,050, filed on Mar. 4, 2013.

(51) Int. Cl.
| | |
|---|---|
| A61P 39/00 | (2006.01) |
| A61P 35/00 | (2006.01) |
| A61K 31/277 | (2006.01) |
| A61K 31/5377 | (2006.01) |
| A61K 38/30 | (2006.01) |
| A61K 31/47 | (2006.01) |
| A61K 31/53 | (2006.01) |
| A61K 31/497 | (2006.01) |
| A61K 31/4985 | (2006.01) |
| A61K 31/357 | (2006.01) |
| A61K 39/395 | (2006.01) |
| A61N 5/10 | (2006.01) |
| A61K 39/00 | (2006.01) |

(52) U.S. Cl.
CPC .......... *A61K 31/277* (2013.01); *A61K 31/357* (2013.01); *A61K 31/47* (2013.01); *A61K 31/497* (2013.01); *A61K 31/4985* (2013.01); *A61K 31/53* (2013.01); *A61K 31/5377* (2013.01); *A61K 38/30* (2013.01); *A61K 39/3955* (2013.01); *A61N 5/10* (2013.01); *A61P 35/00* (2018.01); *A61P 39/00* (2018.01); *A61K 2039/505* (2013.01); *A61K 2039/57* (2013.01)

(58) Field of Classification Search
CPC ................................. A61P 35/00; A61P 39/00
See application file for complete search history.

(56) References Cited

U.S. PATENT DOCUMENTS

| | | | | |
|---|---|---|---|---|
| 2008/0267905 | A1* | 10/2008 | Zeldis | A61K 31/40 424/85.2 |
| 2009/0175868 | A1* | 7/2009 | Ludwig | C07K 16/2863 424/138.1 |

FOREIGN PATENT DOCUMENTS

| | | |
|---|---|---|
| WO | 2011/133668 A2 | 10/2011 |
| WO | 2012/106556 A2 | 8/2012 |

OTHER PUBLICATIONS

Haluska et al. 2007. Clinical Cancer Res. 13:5834-5840.*
Valenciano et al 'Role of IGF-1R Receptor in Radiation Response' Translational Oncology, 5(1), p. 1-9, 2012.*
Lewis et al 'UVB-induced Senescence in Human Keratinocytes Requires a Functional Insulin-lie Growth Factor-1 Receptor and p53' Molecular Biology of the Cell, vol. 19, p. 1346-1353, 2008.*
Wen et al., "Tyrphostin AG 1024 modulates radiosensitivity in human breast cancer cells," Br. J. Cancer Dec. 14, 2001;85(12):2017-21. PMID: 11747348. (Year: 2001).*

(Continued)

Primary Examiner — Theodore R. West
(74) Attorney, Agent, or Firm — MH2 Technology Law Group, LLP

(57) ABSTRACT

Accelerated senescence has been shown to occur as a primary response to cellular stresses including DNA damaging agents (e.g., ionizing radiation) and is widely believed to be caused by continuous proliferative signaling in the presence of cell cycle arrest. The present disclosure provides a method of reducing cellular senescence in non-cancerous cells following exposure to ionizing radiation. The method comprises administering to a subject before, after, or concurrently with exposure to ionizing radiation an effective amount of a compound that inhibits activation of an insulin-like growth factor receptor (IGF-1R) or a compound that inhibits a protein involved in an IGF-1R induced signaling cascade. Also provided is a composition for use in reducing cellular senescence in non-cancerous cells following exposure to ionizing radiation, the composition comprising a compound that inhibits activation of an insulin-like growth factor receptor (IGF-1R) or a compound that inhibits a protein involved in an IGF-1R induced signaling cascade.

17 Claims, 10 Drawing Sheets

Specification includes a Sequence Listing.

(56) References Cited

OTHER PUBLICATIONS

Girard et al., "Chemotherapy and targeted agents for thymic malignancies," Expert Rev. Anticancer Ther. May 2012;12(5):685-95. PMID: 22594902. (Year: 2012).*

Matsumoto et al., "The impact of timing of EGFR and IGF-1R inhibition for sensitizing head and neck cancer to radiation," Anticancer Res. Aug. 2012;32(8):3029-35. PMID: 22843870. (Year: 2012).*

Sun et al., "Role of insulin-like growth factor-1 signaling pathway in cisplatin-resistant lung cancer cells," Int. J. Radiat. Oncol. Biol. Phys. Mar. 1, 2012;82(3):e563-72. PMID: 22197230. (Year: 2012).*

\* cited by examiner

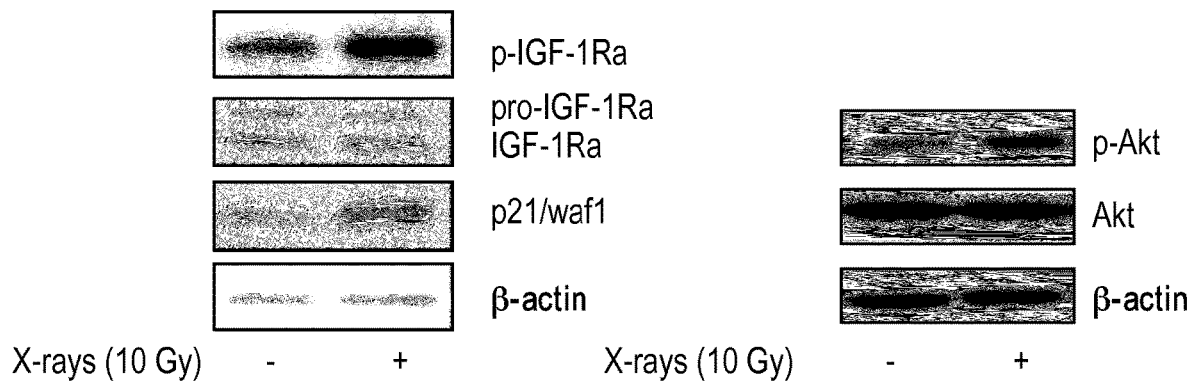
FIG. 2A
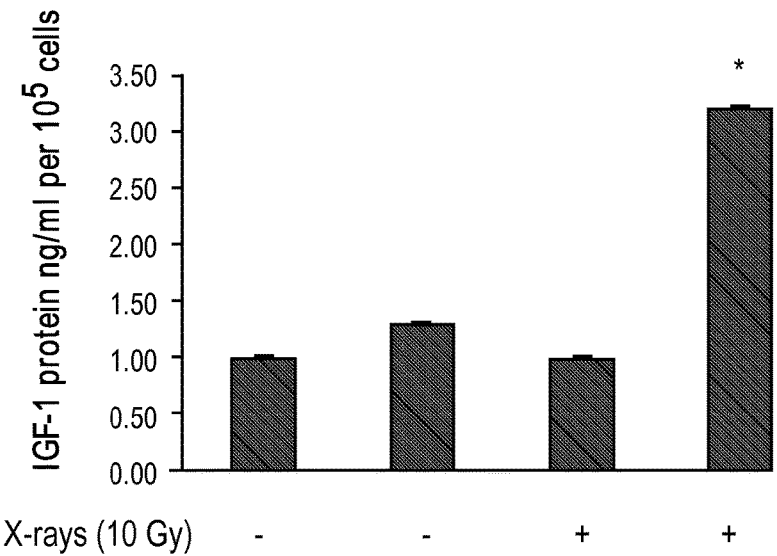
FIG. 2B
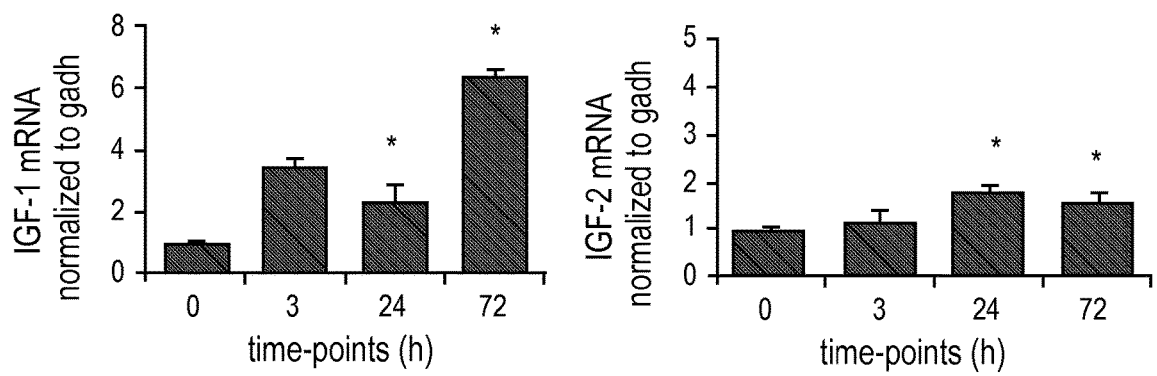
FIG. 2C  FIG. 2D

Control + DMSO / 10 Gy +DMSO / Control + AG1024 / 10 Gy + AG1024

| | | | |
|---|---|---|---|
| 50 Gy | - | - | + | + |
| AG1024 (5µM) | - | + | - | + |

Cleaved caspase-3
Full-length caspase-3
p21/waf1
actin

| | | | |
|---|---|---|---|
| 50 Gy | - | - | + | + |
| IGF-1 (50µg/ml) | - | + | - | + |

Cleaved caspase-3
Full-length caspase-3

METHODS OF INHIBITING IGF-1R ACTIVATION OR DOWNSTREAM SIGNALLING THEREOF TO REDUCE RADIATION-INDUCED CELLULAR SENESCENCE

CROSS REFERENCE TO RELATED APPLICATIONS

This application is a U.S. National Stage application of PCT/US2014/020042 filed 3 Mar. 2014, which claims the benefit of, and relies on the filing date of, U.S. provisional patent application No. 61/772,050, filed 4 Mar. 2013, the entire disclosure of which is incorporated herein by reference.

GOVERNMENT INTEREST

This invention was made with government support under contract number HU0001-10-1-0004 awarded by the Uniformed Services University. The government has certain rights in the invention.

SEQUENCE LISTING

The instant application contains a Sequence Listing which has been submitted electronically in ASCII format and is hereby incorporated by reference in its entirety. Said ASCII copy, created on Feb. 26, 2014, is named HMJ-141-PCT-_SL.txt and is 1,750 bytes in size.

BACKGROUND

Accelerated senescence is a well-recognized cellular response to environmental stresses that damage biological molecules especially DNA. It is characterized by loss of replicative capacity, abnormal gene expression of cell cycle regulators, altered responsiveness to apoptotic stimuli, alterations in cellular morphology, induction of senescence associated secretory proteins, and increased senescence-associated beta-galactosidase (SA-β-gal) activity (Muller 2009). An accumulating body of evidence implicates a role for cellular senescence in aging, especially in age-related tissue and organ dysfunction, possibly through the depletion of functional cells required for organ homeostasis and though induction of inflammation associated with the secretory phenotype (Campisi 2005; Jeyapalan, Ferreira et al. 2007; Muller 2009).

Recent studies suggest that accelerated senescence occurs as the result of proliferative signaling in the presence of a cell cycle checkpoint blockade, often p21/wafl (Demidenko and Blagosklonny 2008; Blagosklonny 2011). The mammalian target of rapamycin (mTOR), a cytoplasmic kinase that is widely regarded as a central integration point for a number of cell signaling pathways including cell proliferation and homeostasis (Laplante and Sabatini 2012), has been identified as a central molecular target for the inhibition of aging-associated senescence as well as stress-induced cellular senescence (Demidenko and Blagosklonny 2008; Anisimov, Zabezhinski et al. 2011; Blagosklonny 2011; Blagosklonny 2011). Treatment with rapamycin, an mTOR inhibitor, prevents accelerated senescence in cells exposed to DNA-damaging agents (Demidenko and Blagosklonny 2008; Leontieva, Demidenko et al. 2011). Similarly, paradoxically, both mitogen activated protein kinase (MAPK) p42/p44 and phosphatidylinositol-3-kinase (PI3K)/Akt signaling pathways which play roles in cell survival and proliferation have also been shown to positively regulate the development of senescence (Boucher, Jean et al. 2004; Miyauchi, Minamino et al. 2004; Nogueira, Park et al. 2008). Akt deficiency causes resistance to replicative- and stress-induced premature senescence while its activation induces premature senescence via increased production of reactive oxygen species (Nogueira, Park et al. 2008). On the other hand, MAPK p42/p44 mediates thrombopoeitin-induced senescence during megarkaryocitic maturation (Besancenot, Chaligne et al. 2010). Both signaling pathways appear to require increased expression of the cell cycle checkpoint protein p21/wafl for the induction of cellular senescence (Besancenot, Chaligne et al. 2010; Astle, Hannan et al. 2012).

Investigation into receptor signaling pathways that contribute to aging-associated cellular senescence has revealed the possible involvement of the insulin like growth factor-1 receptor (IGF-1R) (Holzenberger, Dupont et al. 2003; Lewis, Yi et al. 2008). IGF-1R is a single transmembrane tyrosine kinase receptor whose ligands include IGF-1 and IGF-2 (Valenciano, Henriquez-Hernandez et al. 2012). The activation of IGR-1R involves autophosphorylation of its intracellular domain, followed by recruitment of docking intermediates including the insulin-receptor substrate-1 (IRS-1), which in many cell types leads to activation of PI3K/Akt, MAPK, and mTOR (LeRoith, Baserga et al. 1995; LeRoith, Neuenschwander et al. 1995; Oldham and Hafen 2003; Riedemann and Macaulay 2006) As a growth factor receptor, IGF-1R is known to play a role in cell growth and proliferation under normal conditions and is widely expressed in most transformed cells, conferring pro-survival properties upon stress application (Werner, Re et al. 1993; Dricu, Carlberg et al. 1997; Dricu, Wang et al. 1997; Oldham and Hafen 2003). In agreement with the hypothesis that IGF-1R acts as a mediator of cell survival and proliferation, a number of studies showed a positive correlation between activation of IGF-1R and radiation resistance in some cells (Turner, Haffty et al. 1997; Cosaceanu, Budiu et al. 2007; Qiu, Leibowitz et al. 2010; Floratou, Giannopoulou et al. 2012). However, most of these studies were focused only on the contribution of apoptosis, including in transformed and tumor cells, and it is likely that IGF-1R operates on other modes of radiation-induced cellular response depending on the cellular context. Moreover, the anti-apoptotic activity of IGF-1R is dispensable in the induction of radiation resistance in some tumor cells suggesting the possibility of an unidentified mechanism (Tezuka, Watanabe et al. 2001). Although the IGF-1,-2/IGF-1R signaling axis is known to promote cell proliferation and survival under most circumstances, IGF-1R was recently implicated in several models of senescence. IGF-1R expression levels increased during the development of in vitro replicative senescence in primary cortical neurons (Costantini, Lorenzetto et al. 2010). UVB-induced premature senescence was found to require functional IGF-1R in human keratinocytes (Lewis, Yi et al. 2008). IGF-1 also enhanced senescence in primary cell cultures via a mechanism that involved increased reactive oxygen species (ROS) generation leading to induction of the p53/p21 pathway (Handayaningsih, Takahashi et al. 2012). In mouse embryonic fibroblasts, treatment with IGF-1 inhibited the DNA deacetylase activity of Sirtuin 1 (SIRT1) and promoted stability of p53, ultimately leading to induction of senescence (Tran 2008).

In our previous studies, we determined that accelerated senescence is the primary response of normal bovine pulmonary artery endothelial cells (PAEC) to X-ray exposure (Panganiban, Mungunsukh et al. 2012; Panganiban and Day, 2013 unpublished results). We now provide evidence for the involvement of IGF-1R in the development of radiation-induced accelerated senescence phenotype in primary human lung endothelial cells and primary human kerotinocytes. Our results suggest that IGF-1R signaling is required for X-ray-induced accelerated senescence in endothelial cells and keratinocytes.

SUMMARY

One aspect is directed to a method of reducing cellular senescence in non-cancerous cells following exposure to ionizing radiation, the method comprising administering to a subject before, after, or concurrently with exposure to ionizing radiation a compound that inhibits activation of an insulin-like growth factor receptor (IGF-1R) or a compound that inhibits a protein involved in an IGF-1R induced signaling cascade, wherein the compound is administered in an amount effective to reduce cellular senescence in non-cancerous cells in the subject.

In one embodiment, the non-cancerous cells are endothelial cells. In one embodiment, the endothelial cells are lung or skin cells. In another embodiment, the non-cancerous cells are keratinocytes.

In one embodiment, the compound that inhibits activation of the IGF-1R is an IGF-1R inhibitor. In another embodiment, the compound that inhibits activation of the IGF-1R is an IGF-1 inhibitor or an IGF-2 inhibitor. In a preferred embodiment, the IGF-1 inhibitor is PPP.

In one embodiment the compound that inhibits activation of an IGF-1R or the compound that inhibits a protein involved in an IGF-1R induced signaling cascade is an antibody. In a preferred embodiment, the antibody binds to IGF-1R.

In one embodiment, the IGF-1R inhibitor is BMS 754807; OSI-906; figitumumab (TP-751871); NT52; INSM-18; NVP-AEW541; NVP-ADW742; aIR3; IGF1R scFv-Fc; 486/STOP; 950/STOP; N-(2-methoxy-5-chlorophenyl)-N'-(2-methylquinolin-4-yl)-urea; BMS-754807; IGF-IRi; AG1024; R1507; AXL-1717; picropodophyllotoxin; PQ401; dalotuzumab; A-928605; KW-2450; BMS-536924; IMC-Al2; CP-751871; n-(5-chloro-2-methoxyphenyl)-N'-(2-methoxyquinolin-4-yl)-urea; TAE226; BMS-554417; MK-0646; BMS-536924; MAE87; XL 228; AGL 2263; 1-OMe-AG538; AG538; OSI-868; BMS-754807; ADW742; NVP-ADW642; R1507; MK-0646; A928605; MAB391; BMS-536942; IMC-Al2; rhIGFBP3, ANT-429, ATL-1101, BVP-51004, JV-1-38, pegvisomant, A-928605, or PPP (CAS 477-47-4). In a preferred embodiment the IGF-1R inhibitor is AG1024.

In one embodiment, the compound that inhibits a protein involved in an IGF-1R induced signaling cascade is a PI3K inhibitor or an IRS-1 inhibitor. In one embodiment, the PI3K inhibitor is LY-294002, Wortmannin, BEZ235 (NVP-BEZ235), GDC-0941, PI-103, BKM120 (NVP-BKM120), CAL-101 (GS-1101), IC-87114, GSK2636771, TG 100713, BYL719, PI3K/HDAC inhibitor 1, 3-Methyladenine, YM201636, NVP-BGT226, BAY80-6946, PF-04691502, PKI-402, CH5132799, GDC-0980 (RG7422), NU 7026, NU 7441 (KU-57788), AS-252424, AS-604850, AS-041164, CAY10505, GSK2126458, A66, PF-05212384 (PKI-587), PIK-294, PIK-293, XL765, PIK-93, AZD6482, AS-605240, GSK1059615, TG100-115, PIK-75, PIK-90, TGX-115, TGX-221, XL147, ZSTK474, quercetin, tetrodotoxin citrate, thioperamide maleate, PI10 3. (−)-deguelin, OSU03012, tandutinib, GSK690693, KU-55933, MK-2206, perifosine, triciribine, PI 828, WHI-P 154, compound 15e, 17-P-hydroxywortmannin. Pp 121, PX-478, PX-866, PX-867, WAY-266176, WAY-266175, SF1126, 07-112, IC-486068, and LME00084. In a preferred embodiment, the PI3K inhibitor is LY-294002.

In one embodiment, the subject has cancer and the compound that inhibits activation of an insulin-like growth factor receptor (IGF-1R) or the compound that inhibits a protein involved in an IGF-1R induced signaling cascade is administered before, after, or concurrently with exposure to ionizing radiation to protect non-cancerous cells in the subject from radiation-induced cellular senescence.

In another embodiment, the compound that inhibits a protein involved in an IGF-1R induced signaling cascade is administered no more than 14, 7, 6, 5, 4, 3, 2, or 1 days before or after the subject is exposed to ionizing radiation.

In yet another embodiment, the compound that inhibits activation of an insulin-like growth factor receptor (IGF-1R) or the compound that inhibits a protein involved in an IGF-1R induced signaling cascade is administered concurrently with exposure to ionizing radiation.

In one embodiment, the subject has been accidently exposed to ionizing radiation (e.g., nuclear accident or terrorist attack).

In one embodiment, the subject is a mammal, preferably a human.

Another aspect is directed to a composition for use in reducing cellular senescence in non-cancerous cells following exposure to ionizing radiation, the composition comprising a compound that inhibits activation of an insulin-like growth factor receptor (IGF-1R) or a compound that inhibits a protein involved in an IGF-1R induced signaling cascade.

BRIEF DESCRIPTION OF THE FIGURES

FIG. 1A shows the dose-response effect of increasing X-ray doses in HPAEC on SA-β-gal activity. At 4 days post-irradiation, irradiated and sham-irradiated HPAEC were assayed for SA-β-gal activity. Percentage of SA-β-gal positive cells was counted in at least 3 random fields. Graph represents means±SEM, n=3. * indicates statistical significance from controls, p<0.05. Figure B shows an image of SA-β-gal stained HPAEC following irradiation (10 Gy) or sham irradiation (control). FIG. 1C shows a time-course of p21/wafl upregulation as measured by western blotting at indicated time-points post-irradiation.

FIGS. 2A-D. Induction of IGF-1R signaling in irradiated HPAEC. FIG. 2A shows Western blotting for expressions of proteins involved in IGF-1R hyperphosphorylation (left panel) and Akt hyperphosphorylation (Ser 473, right panel) at 3 hours post-irradiation. FIG. 2B shows IGF-1 levels in secreted medium measured by ELISA at indicated time points post-irrradiation. Graph represents means±SD, n=3. *indicates statistical significance from controls, p<0.05. FIG. 2C shows IGF-1 mRNA levels and FIG. 2D shows IGF-2 mRNA levels in irradiated HPAEC, as assessed by qPCR at indicated time-points post-irradiation. The mRNA levels were normalized to GAPDH. Graph represents means±SD, n=3.* indicates statistical significance from controls, p<0.05.

FIG. 3A shows representative images of SA-β-gal staining at 4 days post-irradiation. FIG. 3B shows the percentage of SA-β-gal positive cells that were counted in at least 3 random fields. Graph represents means±SEM, n=6. * indicates statistical significance from controls, p<0.05. FIG. 3C shows a representative western blot for p53 and p21/wafl expression post-irradiation at indicated time-points in the presence of AG1024 or DMSO.

FIG. 4A are representative images of SA-β-gal staining at 4 days post-irradiation. FIG. 4B shows the percentage of SA-β-gal positive cells that were counted in at least 3 random fields. Graph represents means±SEM, n=6. * indicates statistical significance from controls, p<0.05. FIG. 4C shows a representative western blot for p21/wafl expression post-irradiation at indicated time-points in the presence of AG1024, rapamycin, Ly294002 or DMSO.

FIG. 5A shows a western blot for phosphorylated Akt at 3 hours post-irradiation. FIG. 5B shows a western blot for phosphorylated-S6 (Ser235/236) at 72 hours post-irradiation.

FIGS. 8A and 8B show the upregulation of p21/waf in lung tissue by western blot following exposure to radiation at the indicated times. FIG. 8C shows the upregulation of phosphorylated IGF-1R in the lung at 24 hours post radiation. Blots were stripped and reprobed for β-actin as a loading control.

In FIG. 9A, qPCR was performed to determine the levels of IGF-1 mRNA at indicated time-points post-irradiation. The mRNA levels were normalized to GAPDH. Bars indicate mean±SD, n=3. * indicates statistical significance from control, p <0.05. In FIG. 9B, whole cell lysates were prepared at indicated time points and the level of phosphorylated IGF-1R was detected by western blot analysis. Blots were stripped and probed for β-actin as a loading control. Experiments were repeated at least 3 times, and representative data are shown.

In FIG. 10A, keratinocyte cell lysates were prepared at 24 hours post-irradiation and blotted for p21/waf, with β-actin as a loading control. In FIG. 10B, keratinocytes were assayed for the expression of SA-β-gal at 72 hours post irradiation. Bars are means±SD; * indicates significance from control, p<0.05., n=3.

IGF1R Inhibitors

Figure 1A:
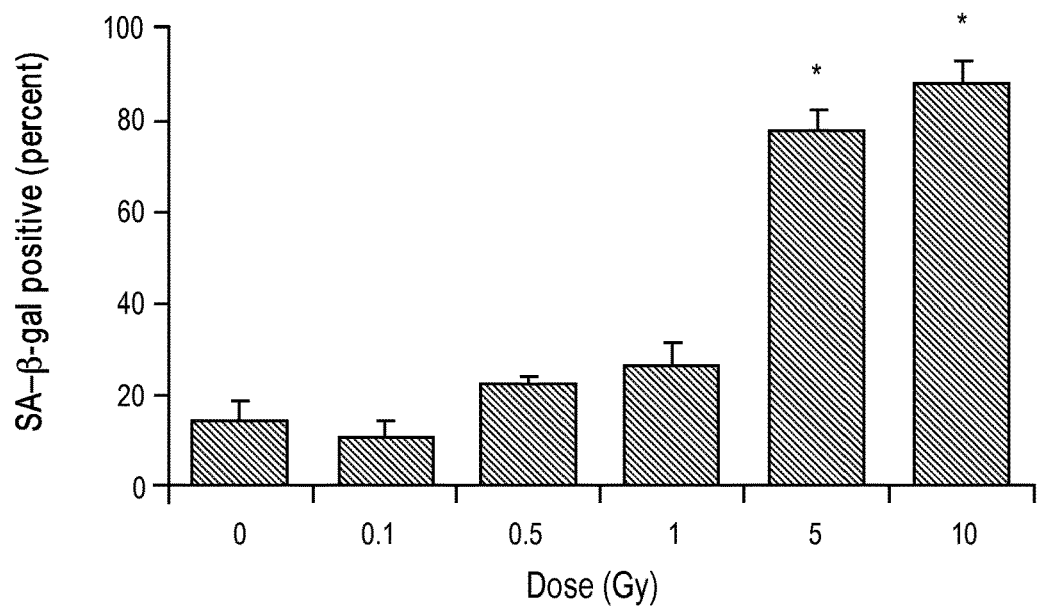
FIGS. 1A-C. X-rays induce accelerated senescence in HPAEC. Subconfluent HPAEC were exposed to indicated doses of X-rays and then incubated until time of assay.

The methods and compositions disclosed in s application involve one or more RIF-1R inhibitors. An IGF-1R inhibitor decreases the biological activity (e.g., kinase activity) of an IGF-IR protein. An IGF-RI inhibitor may be an antibody or a small compound. A variety of TGF-1R inhibitors are known in the art. Non-limiting examples of IGF-1R inhibitors include: BMS 754807; OSI-906; figitumumab (CP-751871); NT52; INSM-18; NVP-AEW541; NVP-ADW742; aIR3; IGF1R scFv-Fc; 486/STOP; 950/STOP; N-(2-methoxy-5-chlorophenyl)-N'-(2-methylquinolin-4-yl)-urea; BMS-754807; IGF-IRi; AG1024; R1507; AXL-1717; picropodophyllotoxin; PQ401; dalotuzumab; A-928605; KW-2450; BMS-536924; IMC-Al2; CP-751871; n-(5-chloro-2-methoxyphenyl)-N'-(2-methoxyquinolin-4-yl)-urea; TAE226; BMS-554417; MK-0646; BMS-536924; MAE87; XL 228; AGL 2263; I-OMe-AG538; AG538; OSI-868; BMS-754807; ADW742; NVP-ADW642; R1507; MK-0646; A928605; MAB391; BMS-536942; IMC-Al2; rhIGFBP3, ANT-429, ATL-1101, BVP-51004, JV-1-38, pegvisomant, A-928605, or PPP (CAS 477-47-4).

In one embodiment, the IGF-1R inhibitor is AG1024. AG1024, also known as 3-bromo-5-tert-butyl-4-hydroxy-benzylidene)malononitrile, is a small molecule having a molecular formula of $C_{14}H_{13}BrN_2O$ and an approximate molecular weight of 305.17.

In another embodiment, the IGF-1R inhibitor is PPP (CAS 477-47-4). PPP (CAS 477-47-4), also known as picropodophyliin, is a small molecule having a molecular formula of $C_{22}H_{22}O_8$ and an approximate molecular weight of 414.4.

Additional examples of IGF-1R inhibitors are described in U.S. Pat. Nos. 7,638,621; 7,638,605; 7,605,272; 7,521,453; 7,432,244; and 6,071,891 (each herein incorporated by reference); and U.S. Patent Application Publication Nos. 2010/0028342; 2009/0099229; 2009/0099133; 2009/0054508; 2008/0025990; 2008/0161278; 2008/0152649; 2007/0185319; 2007/0275922; 2007/0129399; 2007/0123491; 2005/0054638; and 2004/0213792 (each herein incorporated by reference).

Several IGF-1R inhibitors are commercially available. Standard doses for IGF-1R inhibitors are known in the art and can range from 0.1 mg to 300 mg (e.g., 0.1 mg to 200 mg, 0.1 mg to 150 mg, 0.1 ing to 100 mg, and 1.0 mg to 50 mg) for each individual IGF-1R inhibitor.

PI3K Inhibitors

The methods and compositions disclosed in this application may involve one or more PI3K inhibitors. A PI3K inhibitor decreases the biological activity (e.g., kinase activity) of a PI3K protein. A PI3K inhibitor may be an antibody or a small compound. A variety of PI3K inhibitors are known in the art. Non-limiting examples of PI3K inhibitors include: LY-294002, Wortmannin, BEZ235 (NVP-BEZ235), GDC-0941, PI-103, BKM120 (NVP-BKM120), CAL-101 (GS-1101), IC-87114, GSK2636771, TG 100713, BYL719, PI3K/HDAC inhibitor 1, 3-Methyladenine, YM201636, NVP-BGT226, BAY80-6946, PF-04691502, PKI-402, CH5132799, GDC-0980 (RG7422), NU 7026, NU 7441 (KU-57788), AS-252424, AS-604850, AS-041164, CAY10505, GSK2126458, A66, PF-05212384 (PKI-587), PIK-294, PIK-293, XL765, PIK-93, AZD6482, AS-605240, GSK1059615, TG100-115, PIK-75, PIK-90, TGX-115, TGX-221, XL147, ZSTK474, quercetin, tetrodotoxin citrate, thioperamide maleate, PI103, (−)-degiielin, OSUO3012, tandutinib, GSK690693, KU-55933, MK-2206, perifosine, triciribine, PI 828, WII-P 154, compound 15e,17-P-hydroxywortmannin, Pp 121, PX-478, PX-866, PX-867, WAY-266176, WAY-266175, SF1126, 07412, LC-486068, and LME00084.

In one embodiment, the PI3K inhibitor is LY-294002. LY-294002, also known as 2-(4-Morpholinyl)-8-phenyl-4H-chromen-4-one, is a small molecule having a molecular formula of $C_{19}H_{17}NO_3$ and an approximate molecular weight of 307.34.

Additional PI3K inhibitors are described in U.S. Pat. Nos. 6,100,090; 6,908,932; 7,598,377; and 7,666,901 (each herein incorporated by reference); and U.S. Patent Application Publication Nos. 2010/0069629; 2010/0034786; 2010/0029693; 2010/0022534; 2010/0016306; 2009/0325954; 2009/0318411; 2009/0247567; 2009/0233926; 2009/0227587; 2009/0118336; 2008/0319021; 2008/0269210; 2008/0242665; 2008/0085997; 2008/0039459; 2008/0132502; 2008/0014598; 2008/0287469; 2007/0244312; 2007/0238745; 2006/0089320; 2006/0026702; 2006/0084697; 2005/0272682; 2004/0077580; 2004/0063657; 2003/0182669; 2003/0158212; 2003/0149074; 2003/0225013; and 2003/0055018 (each herein incorporated by reference).

Several PINK inhibitors are commercially available. Standard doses for PI3K inhibitors are known in the art and can range from 0.1 mg to 300 mg (e.g., 0.1 mg to 200 mg, 0.1 mg to 150 mg, 0.1 mg to 100 mg, and 1.0 mg to 50 mg) for each individual PI3K inhibitor.

Pharmaceutical compositions comprising the IGF-1R inhibitor or PI3K inhibitor may also contain other active compounds providing supplemental, additional, or enhanced therapeutic functions. In one embodiment, the other active compound is an antibiotic, including, but not limited to, metronidazole, fidaxomicin, or vanomycin. The pharmaceutical compositions may also be included in a container, pack, or dispenser together with instructions for administration.

The pharmaceutical compositions may also further comprise a pharmaceutically acceptable excipient including, but not limited to, a carrier or diluent, such as a gum, a starch (e.g. corn starch, pregeletanized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof; a binder (e.g. acacia, cornstarch, gelatin, carbomer, ethyl cellulose, guar gum, hydroxypropyl cellulose, hydroxypropyl methyl cellulose, povidone); a disintegrating agent (e.g. cornstarch, potato starch, alginic acid, silicon dioxide, croscarmelose sodium, crospovidone, guar gum, sodium starch glycolate), a buffer (e.g. Tris-HCl, acetate, phosphate) of various pH and ionic strength; and additive such as albumin or gelatin to prevent absorption to surfaces; a detergent (e.g. Tween 20, Tween 80, Pluronic F68, bile acid salts); a protease inhibitor; a surfactant (e.g. sodium lauryl sulfate); a permeation enhancer; a solubilizing agent (e.g. glycerol, polyethylene glycerol); an anti-oxidants (e.g. ascorbic acid, sodium metabisulfite, butylated hydroxyanisole); a stabilizer (e.g. hydroxypropyl cellulose, hydroxypropylmethyl cellulose); a viscosity increasing agent (e.g. carbomer, colloidal silicon dioxide, ethyl cellulose, guar gum); a sweetener (e.g. aspartame, citric acid); a preservative (e.g. Thimerosal, benzyl alcohol, parabens); a lubricant (e.g. stearic acid, magnesium stearate, polyethylene glycol, sodium lauryl sulfate); a flow-aid (e.g. colloidal silicon dioxide), a plasticizer (e.g. diethyl phthalate, triethyl citrate); an emulsifier (e.g. carbomer, hydroxypropyl cellulose, sodium lauryl sulfate); a polymer coating (e.g. poloxamers or poloxamines); a coating and film forming agent (e.g. ethyl cellulose, acrylates, polymethacrylates); an adjuvant; a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters such as ethyl oleate) solution, suspension, emulsion or oil; and a parenteral vehicle (for subcutaneous, intravenous, intraarterial, or intramuscular injection), including but not limited to, sodium chloride solution, Ringer's dextrose, dextrose and sodium chloride, lactated Ringer's and fixed oils.

Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

A pharmaceutical composition of the invention is formulated to be compatible with its intended route of administration. Methods to accomplish the administration are known to those of ordinary skill in the art. This includes, for example, injections, by parenteral routes such as intravenous, intravascular, intraarterial, subcutaneous, intramuscular, intraperitoneal, intraventricular, intraepidural, or others as well as oral, nasal, ophthalmic, rectal, or topical. Sustained release administration is also specifically contemplated, by such means as depot injections or erodible implants. Localized delivery is particularly contemplated, by such means as delivery via a catheter to one or more arteries, such as the renal artery or a vessel supplying a localized site of interest.

By "subject" is meant any animal. Animals that can be treated using the methods and compositions of the invention include humans, horses, dogs, cats, pigs, goats, rabbits, hamsters, monkeys, guinea pigs, rats, mice, lizards, snakes, sheep, cattle, fish, and birds.

As will be appreciated in the art, an amount of the compound effective to reduce cellular senescence in non-cancerous cells in the subject varies depending upon the manner of administration, the age, body weight, and general health of the patient. Ultimately, the prescribers will decide the appropriate amount and dosage rezimen. Additionally, an effective amount may be that amount of compound that is safe and efficacious in reducing cellular senescence in non-cancerous cells as determined and approved by a regulatory authority (such as the U.S. Food and Drug Administration).

Compounds useful in the invention include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein.

In one embodiment, the subject has cancer and the compound is administered to the subject before, after, or concurrently with exposure to ionizing radiation. Non-limiting examples of cancer include: acute lymphoblastic leukemia, acute mytdoid leukemia, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, cervical cancer, chordoma, chronic lymphocytic leukemia, chronic myeloproliferative disorder, colon cancer, colorectal cancer, craniopharyngioma, cutaneous T-cell lymphoma, endometrial cancer, ependymoblastoma, ependymoma, esophageal cancer, Ewing sarcoma, extracranial germ cell tumor, extragonadal germ cell tumor, extrahepatic bile duct cancer, eye cancer, gallbladder cancer, gastric cancer, gastrointestinal cancer, germ cell tumor, gestational trophoblastic tumor, glioma, hairy cell leukemia, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, acute lymphoblatic leukemia, chronic lymphocytic leukemia, lip and oral cavity cancer, liver cancer, lung cancer, non-Hodgkin lymphoma, macro globulinemia, osteosarcoma, medulloblastoma, melanoma, merkel cell carcinom, mesothelioma, mouth cancer, mycosis fungiodes, myelodysplasia syndrome, multiple myeloma, nasal cavity and paranasal sinus cancer, nasopharyngeal cancer, non-small cell lung cancer, oral cancer, oropharyngeal cancer, osteosarcoma, ovarian cancer, ovarian epithelial cancer, pancreatic cancer, papillornatosis, parathyroid cancer, penile cancer, pharyngeal cancer, pituitary tumor, prostate cancer, rectal cancer, renal cell cancer, retinoblastoma, rhabdomycosarcoma, salivary gland cancer, sarcoma, skin cancer, small cell lung cancer, small intestine cancer, soft tissue sarcoma, testicular cancer, throat cancer, thotnoma, thymic carcinoma, thyroid cancer, urethral cancer, uterine cancer, vaginal cancer, and Wilms tumor.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Materials and Methods:
Cell Culture and Reagents. Human pulmonary artery endothelial cells (HPAEC) were obtained from Cell Applications, Inc. (San Diego, Calif.) and cultured in EBM-2 basal medium containing supplements and growth factors as indicated in the manufacturer's protocol (Lonza, Walkersville, Md.). Cells were maintained at 37° C. in a humidified atmosphere containing 5% $CO_2$. Subconfluent HPAEC at passages 4-8 were used for all experiments. The following chemical inhibitors and their final concentrations were used: AG1024 (5 µM, EMD Millipore, Billerica, Mass.), U0126 (10 µM), Ly294002 (20 µM), rapamycin (500 nM). Each inhibitor was dissolved in DMSO and added to cell cultures so that the final concentration of the solvent did not exceed 0.1%. 20 mM N-acetyl cysteine (NAC) was dissolved in distilled $H_2O$.

Cell Irradiation: HPAEC were either irradiated or sham-irradiated at subconfluence (70-90%). Irradiations were conducted using RS2000 Biological Irradiator (Rad Source Technologies, Alpharetta, Ga.) with 0 3 mm Cu shielding at a dose rate of 2.4 Gy/min (160 kV, 25 mA) at room temperature.

Western blotting. Whole cell extracts were prepared in RIPA buffer (50 mM Tris HCl pH 8, 150 mM NaCl, 1% NP-40, 0.5% sodium deoxycholate, and 0.1% SDS) supplemented with protease inhibitors (Sigma-Aldrich, St. Louis, Mont.), 1 mM PMSF, 2 mM $Na_3VO_4$ and/or Halt phosphatase inhibitors (Thermo Scientific, Rockford, Ill.) or SDS-laemmli buffer (Bio-Rad, Hercules, Calif.) containing 50 mM DTT. Samples were vortexed, incubated for 10 mM at 4° C., and subjected to sonication (Heat Systems-Ultrasonics Inc., Plainview, N.Y.) for 5 sec at 4° C. Samples were then centrifuged at 14,000×g for 10 min and supernatant was collected.

Protein concentrations from whole cell lysates were determined using Protein® BCA Protein Assay Kit (Thermo Scientific, Rockford, Ill.). Equal amounts of proteins were separated in SDS-PAGE and transferred to PVDF membranes (Thermo Scientific, Rockford, Ill.). For western blotting, the following antibodies were used: anti-phospho-IGF1R, total IGF-1R, anti-p53, anti-p21/wafl, and anti-β-actin (Santa Cruz Biotechnology, Inc., Santa Cruz, Calif.); anti-phospho-S6, anti-phospho-Akt and total Akt (Cell Signaling Technology, Danvers, Mass.). Proteins were detected with horseradish peroxidase-linked secondary antibodies and SuperSignal® West Pico Chemiluminescent Substrate (Pierce, Rockford, Ill.). WCIF ImageJ software was used for densitometry analysis.

Quantitative real-time reverse transcription polymerase chain reaction (qPCR). Total RNA was isolated from cultured cells using the RNeasy Kit (Qiagen, Valencia, Calif.). RNA was quantified spectroscopically (ND-1000 Spectrophotometer, NanoDrop, Wilmington, Del.). RNA (400 ng) was subjected to reverse transcription in a total volume of 20ul. Following dilution 5-fold with water, 2 µl of cDNA was used for 20 µl qPCR reaction. PCR was performed in duplicates using 6 µM of each primer and 10 µl of Sybr-Green® PCR master mix (Applied Biosystems, Foster City, Calif.). The following primers were used for detection of IGF-1: forward 5'-TGC CCA AGA CCC AGA AGT-3' (SEQ ID NO:2) and reverse 5'-CTC CTG TCC CCT CCT TCT GTT-3' (SEQ ID NO:1) and IGF-2: forward 5'-ACA CCC TCC AGT TCG TCT GT-3' (SEQ ID NO:3) and reverse 5'-GAAACAGCACTCCTCAACGA-3' (SEQ ID NO:4). As an internal control, mRNA levels of GAPDH were determined using primers: forward 5'-GAA GCT CGT CAT CAA TGG AAA-3' (SEQ ID NO:5) and reverse 5'-CCA CTT GAT GTT GGC AGG AT-3' (SEQ ID NO:6). For quantification, the comparative threshold cycle (Ct) method was used to assess relative changes in mRNA levels between the untreated (control) and the irradiated samples.

Senescence-associated fl-galactosidase (SA-β-gal) Assay. SA-β-gal assay was performed according to established protocols with minor modifications (Dimri, Lee et al. 1995; Bandyopadhyay, Gatza et al. 2005). To avoid density-dependent false positive expression of SA-β-gal, HPAEC were seeded at a density of $1.0$-$2.0 \times 10^4$ on 12-well or 6-well dishes and allowed to reach 50-70% confluence prior to treatment. At indicated time-points postirradiation, cells were washed twice in ice cold PBS, fixed in 2% formaldehyde/0.2% glutaraldehyde in PBS for 5 min at room temperature and washed again twice in ice-cold PBS. 1.5-2 ml of freshly prepared X-gal staining solution (1 mg/ml of 5-bromo-4-chloro-3-indolyl β-D-galactoside in 40 mM citric acid/sodium phosphate, pH 6.0 (made by mixing 36.85 parts 0.1 M citric acid solution with 63.15 parts 0.2 M sodium phosphate solution and then verifying pH to be 6.0, 0.1M citric acid was added to adjust pH when necessary), 5 mM potassium ferrocyanide, 5 mM potassium ferricyanide, 150 mM NaCl, 2 mM $MgCl_2$) was then added to the culture dishes and the dishes were incubated for 12-20 h at 37° C. (without $CO_2$). After incubation, cells were washed twice in ice-cold PBS and once in methanol and allowed to dry. Cells were examined for perinuclear blue staining indicative of SA-β-gal activity in at least 3 random fields.

Statistics. Means±standard deviations (SD) or error of the mean (SEM) were calculated, and statistically significant differences between two groups were determined by the Student's t test. $p<0.05$ was considered statistically significant.

Results

Figure 1B:
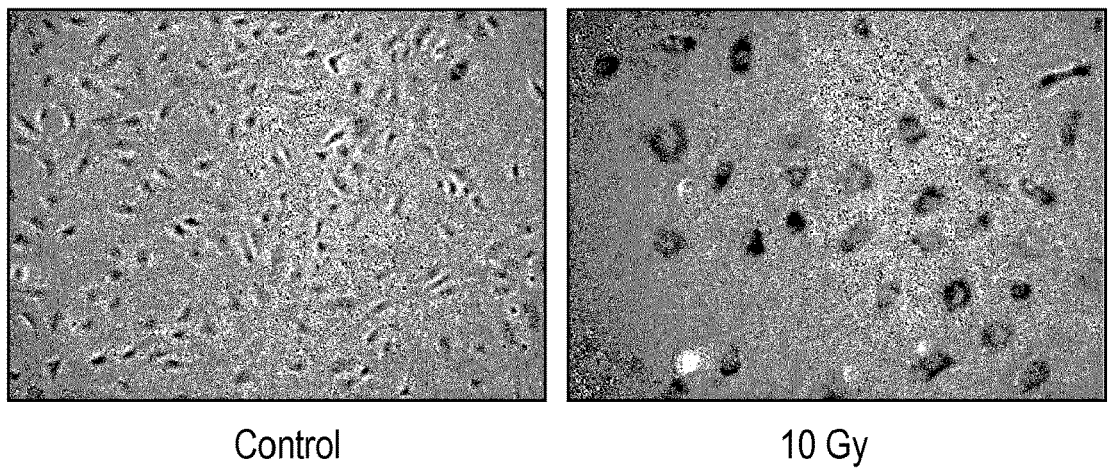
Figure 1C:
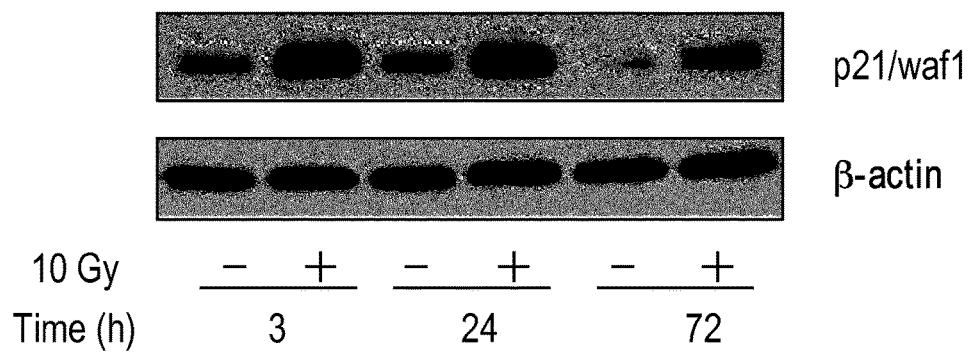

HPAEC undergo accelerated senescence post-irradiation. We previously determined in bovine PAEC that accelerated senescence is the primary cellular response to exposure to 10 Gy X-rays with very limited apoptosis and no detectable necrosis (Panganiban, Mungunsukh et al. 2012). Two salient features of senescence were identified in X-ray-induced senescence in BPAEC—upregulation of p21/wafl and increased SA-β-gal activity. p21/wafl, also known as cyclin-dependent kinase inhibitor 1, is a cell cycle checkpoint protein and contributes to cell cycle arrest, a necessary component of cellular senescence. In contrast, SA-β-gal is a widely used marker for cellular senescence that was first described by Dimri et al (Dimri, Lee et al. 1995) and has routinely been used over the years to detect senescent cells in vitro and in vivo (Freund, Laberge et al. 2012). The function of increased SA-β-gal is not completely understood in senescence cells. We investigated the X-ray effects on the development of senescent phenotype in human PAEC (HPAEC). Our data indicated that HPAEC underwent cellular senescence upon exposure to 10 Gy X-rays as determined by upregulation of p2 l/wafl within 3 hours post-irradiation. Increased SA-β-gal activity, detected cytochemically as blue perinuclear staining, was detected optimally at 4 days post-irradiation (FIG. 1B). X-ray-exposed HPAEC also exhibited changes in cell morphology, displaying unusually large cell size and flattened cytoplasmic appearance compared to sham-irradiated controls (FIG. 1B). We also observed the upregulation of p21/wafl within 3 hours post-irradiation, consistent with inhibition of the cell cycle in advance of senescence (FIG. 1C). These data are consistent with our findings using bovine derived PAEC (Panganiban, Mungunsukh et al. 2012).

Figure 9A:
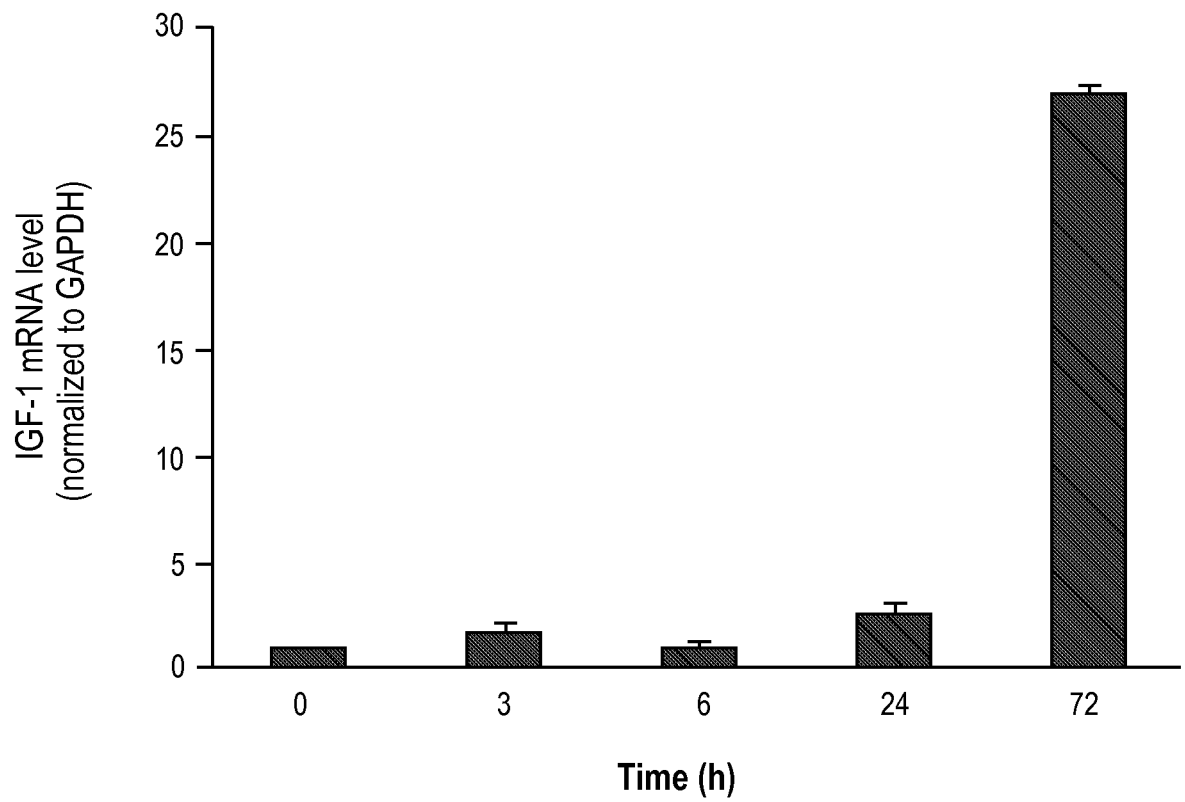
FIGS. 9A-B. X-rays activate the IGF-1R signaling cascade. Subconfluent cultures of HPAEC were either sham irradiated or exposed 10 Gy X-ray irradiation.

X-rays activate the IGF-1R signaling cascade. Exposure to X-rays causes alterations in global gene expression. As we had previously determined that the primary response causing loss of cell viability in pulmonary artery endothelial cells is accelerated senescence, we used a pathway-focused senescence array to examine mRNA and protein changes over time after 10 Gy exposure in HPAEC. Among the genes observed to be altered in expression, IGF-1 mRNA level was increased about 15 fold within 72 hours post-irradiation (data not shown). These results were confirmed using qRT-PCR (about 2 fold at 24 hours post-irradiation and about 6 fold at 72 hours post-irradiation, $p<0.05$, FIG. 2C). A separate qRT-PCR experiment showed that IGF-1 mRNA was increased about 2-fold at 24 hours post-irradiation and about 28-fold at 72 hours post-irradiation (FIG. 9A). Similarly, IGF-2 mRNA was increased (about 1.7 fold at 24 hours post-irradiation and about 1.5 fold at 72 hours post-irradiation, FIG. 2D). IGF-1 can act in paracrine and/or autocrine manner (Clemmons 2009) and in cultured cells it is secreted in the medium once produced (Abboud, Bethel et al. 1991; Khalid, Haresign et al. 2000). ELISA indicated that IGF-1 was increased in the medium 72 hour post-irradiation (about 3.2 fold, $p<0.05$).

These increases in the secretion of IGF-1 and in the gene expressions of both IGF-1 and IGF-2, two known activating ligands of IGF-1R, led us to examine the activation of its receptor (IGF-1R) using western blotting for IGF-1R phosphorylation. Phosphorylation at Y1165 and Y1166 is essential for IGF-1R kinase activation (Lopaczynski et al. 2000; Baserga R. 1999). Phosphorylation at Ser 473 is required for full activation of Akt in a PI3K-dependent manner (Persad S et al. 2001). As shown in FIG. 2A, IGF-1R hyperphosphorylation (left panel) was detected within 3 hours post-irradiation along with Akt hyperphosphorylation (right panel). Interestingly, the increase in phosphorylation of IGF-1R and Akt occurred concurrently with p21/wafl upregulation.

Figure 9B:
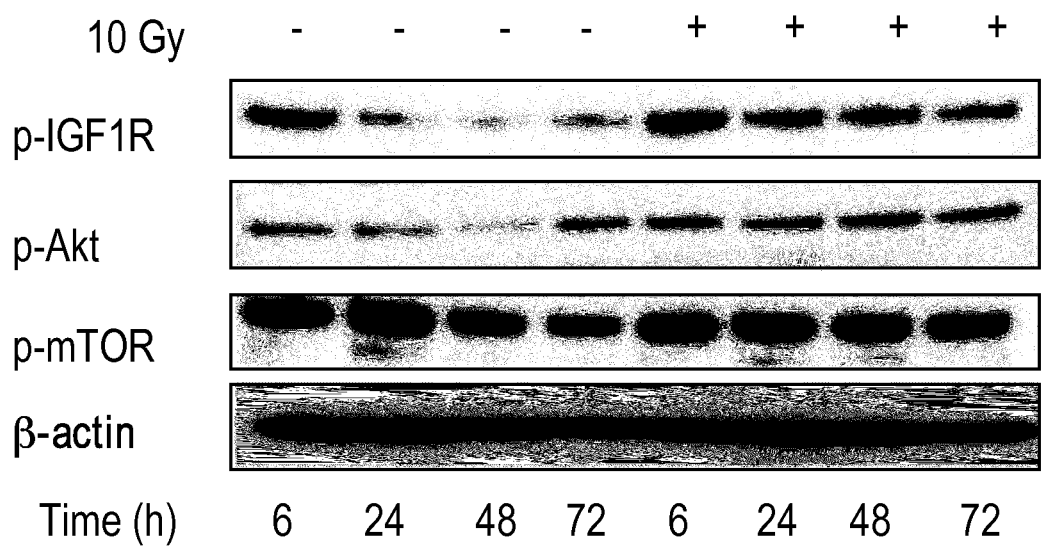

Cell lysates from untreated HPAEC or HPAEC exposed to 10 Gy irradiation were also prepared for western blotting and assayed at various times for expression of phosphorylated IGF-1R, phosphorylated Akt, and phosphorylated mTOR. Blots were stripped and reprobed with β-actin as a loading control. IGF-1R phosphorylation was detected within 6 hours (FIG. 9B).

Figure 3A:
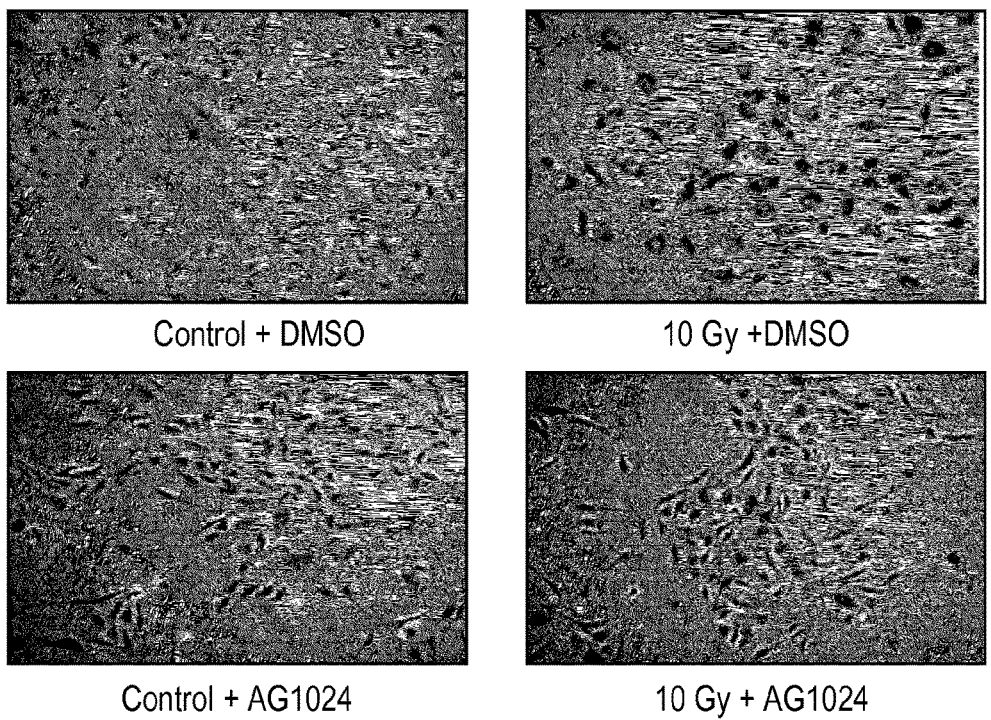
FIGS. 3A-C. Attenuation of radiation-induced accelerated senescence by AG1024. Subconfluent HPAEC were pre-treated with 5 uM AG1024 or vehicle (DMSO) for 30 minutes, exposed to 10 Gy X-rays and then incubated until time of assay.
Figure 3B:
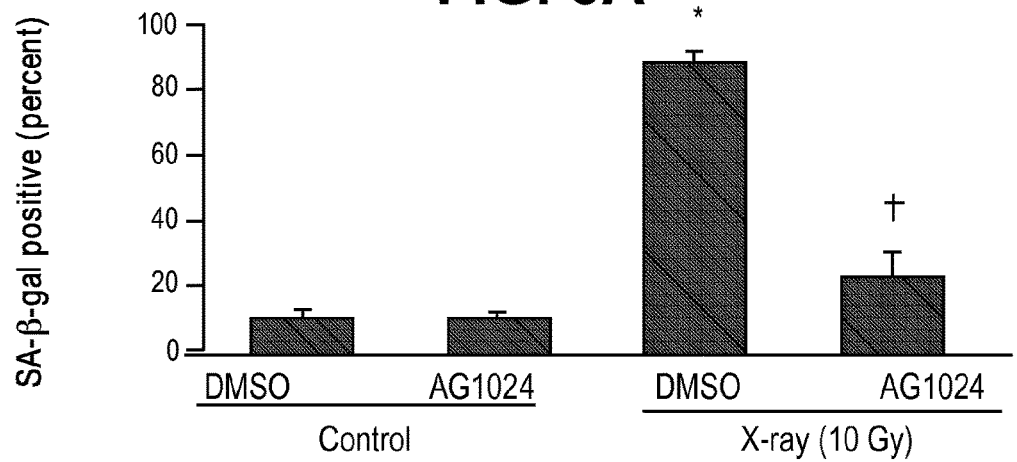
Figure 3C:
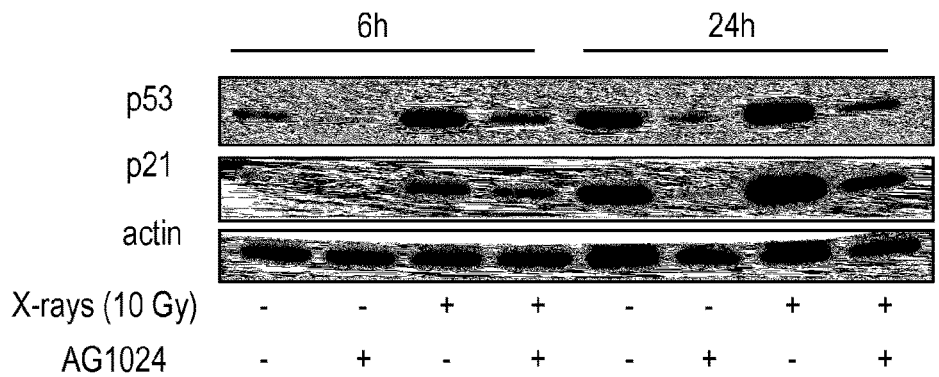

AG1024 blocks radiation-induced accelerated senescence. As X-rays induced IGF-1R phosphorylation, IGF-1 and IGF-2 upregulation as well as accelerated senescence in HPAEC, we hypothesized that IGF-1R activation may function in the development of accelerated senescence post-irradiation. To test this hypothesis, we exposed HPAEC to 10 Gy X-rays in the presence of AG1024 (an IGF-1R inhibitor) and examined cellular senescence Inhibition of IGF-1R prevented the change in cellular volume observed within 96 h of radiation exposure, and cells maintained a more normal morphology (FIG. 3A). Blocking IGF-1R activation significantly reduced cellular senescence as shown by suppression of radiation-induced p53 and p21/wafl and by radiation-induced SA-β-gal activity assay (FIGS. 3B and 3C).

Figure 4A:
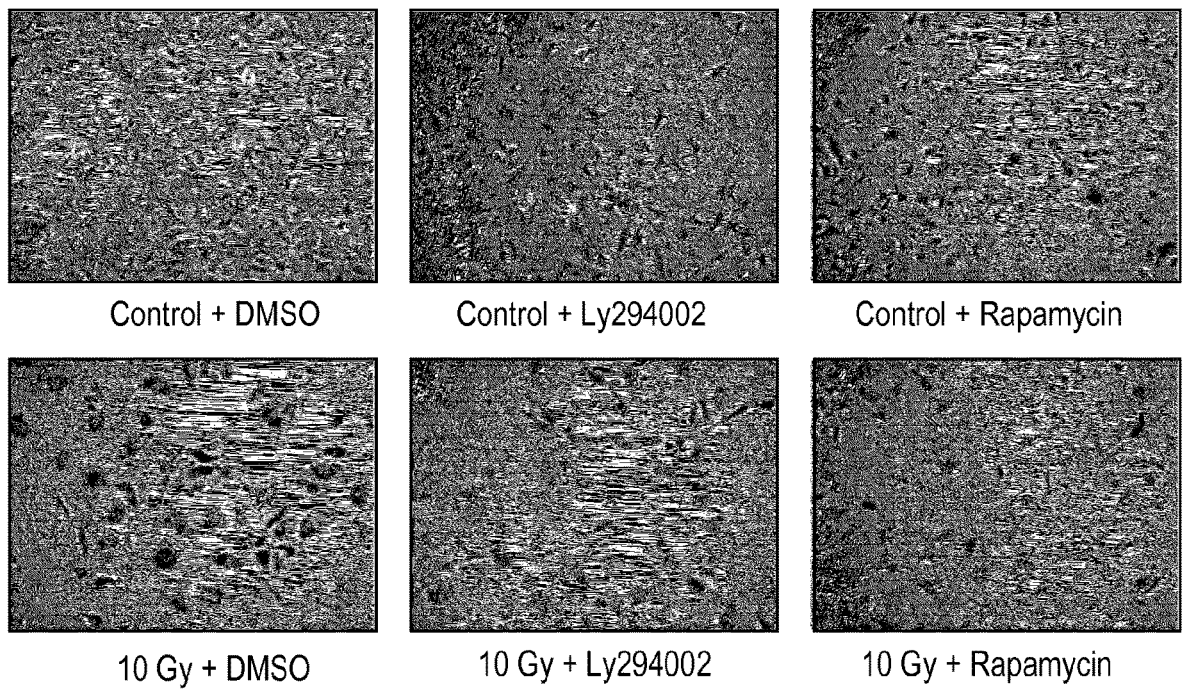
FIGS. 4A-C. Attenuation of radiation-induced accelerated senescence by rapamycin and Ly294002. Subconfluent HPAEC were pretreated with 500 nM rapamycin, 20 uM Ly294002, or vehicle (DMSO) for 30 minutes, exposed to 10 Gy X-rays and then incubated until time of assay.
Figure 4B:
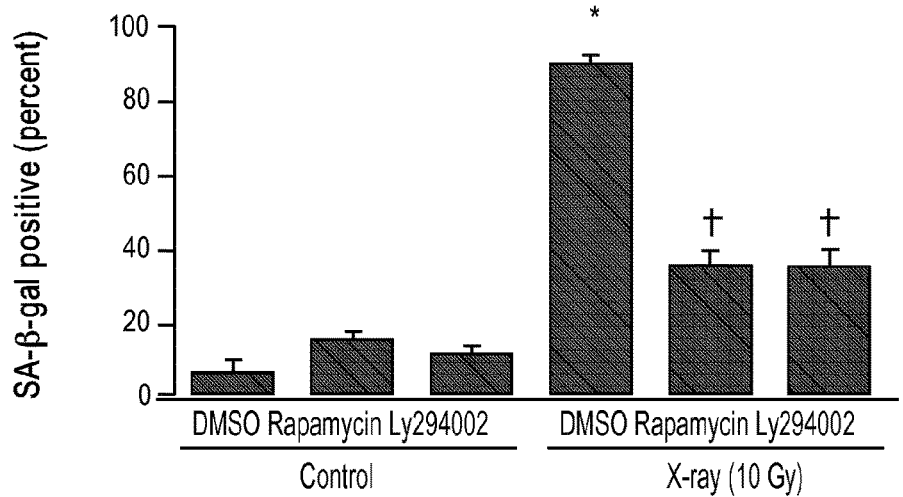
Figure 4C:
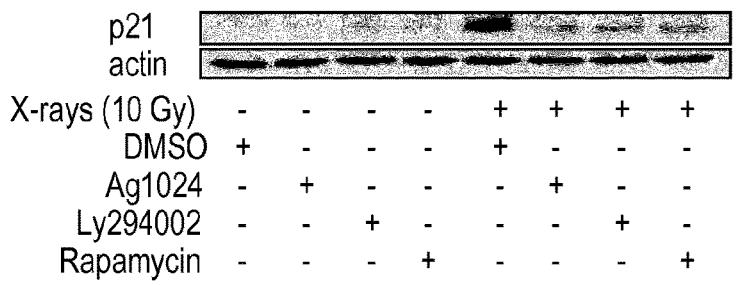

Inhibition of mTOR and PI3K, but not p42/p44 MAPK, blocks radiation-induced accelerated senescence. Recent studies showed that mTOR is required for stress-induced senescence. Treatment with rapamycin prevents the increase in SA-β-gal activity in cells exposed to DNA-damaging agents (Demidenko and Blagosklonny 2008; Leontieva and Blagosklonny 2010; Leontieva, Gudkov et al. 2010) and protects mice from radiation-induced mucositis (Iglesias-Bartolome, Patel et al. 2012). Furthermore, activation of IGF-1R has been demonstrated to cause activation of a signaling cascade via the PI3K/Akt and MAPK pathways which can converge at mTOR (Salatino, Schillaci et al. 2004; Chenal, Pierre et al. 2008) (Rios-Moreno, Jaramillo et al. 2011). We tested whether inhibition of mTOR or PI3K would attenuate IR-induced accelerated senescence in irradiated HPAEC. The mTOR inhibitor rapapmycin and the PI3K inhibitor LY294002 both resulted in the maintenance of normal cellular morphology following 10 Gy X-ray exposure (FIG. 4A). Inhibition of PI3K and mTOR also attenuated radiation-induced SA-β-galactosidase activation (FIGS. 4A and B) and attenuated radiation-induced p21/wafl expression (FIG. 4C). Interestingly, treatment with U0126, a MAPK inhibitor, did not rescue cells from undergoing accelerated senescence (data not shown).

Figure 5A:
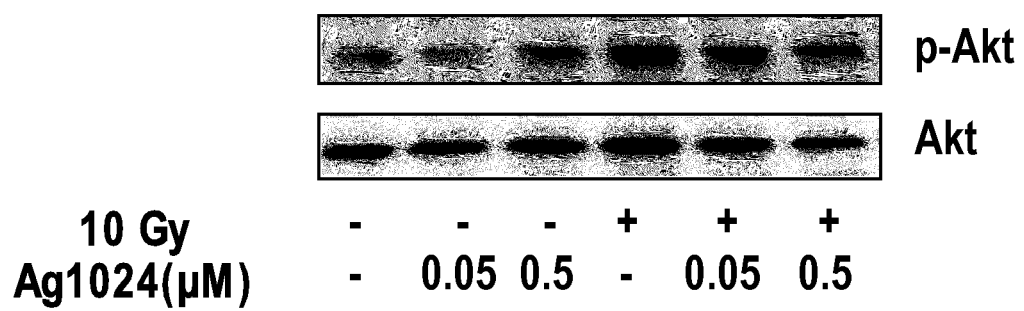
FIGS. 5A-B. IR-induced IGF-1R-mediated accelerated senescence requires intact mTOR. Subconfluent HPAEC were treated with 5 uM AG1024 or DMSO for 30 minutes and subjected to 10 Gy X-rays. Whole cell lysates were prepared for western blotting.
Figure 5B:
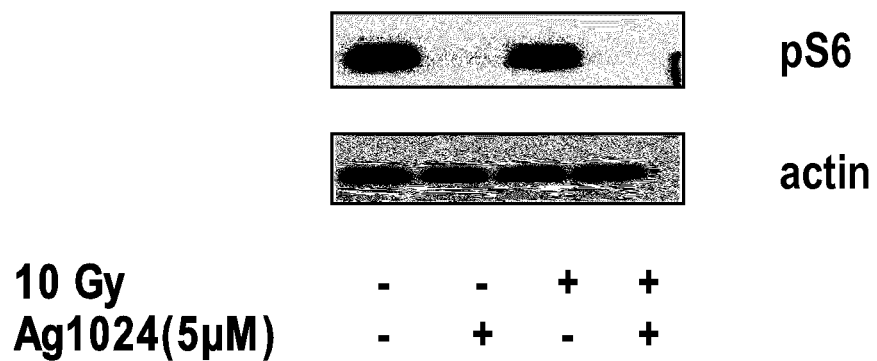

We investigated the dependence of Akt activation by X-ray irradiation on IGF-1R signaling. We found that the inhibition of IGF-1R by AG1024 had no effect on radiation-induced phosphorylation of Akt S473 (unpublished results). To determine whether IGF-1R signaling is upstream of mTOR activation following radiation exposure, we examined the effect of AG1024 on phosphorylation of S6 ribosomal protein (pS6), a known target of S6 kinase which is downstream of activated mTOR (Ferrari S, et al. 1991). AG1024 treatment significantly reduced the phosphorylation of S6 ribosomal protein (Ser 235/236). AG1024 treatment blocks decreased levels of phosho-S6 kinase significantly but not phospo-Akt (FIGS. 5A and 5B), suggesting that intact mTOR activity is required for radiation-induced IGF-1R-mediated accelerated senescence.

Figure 6A:
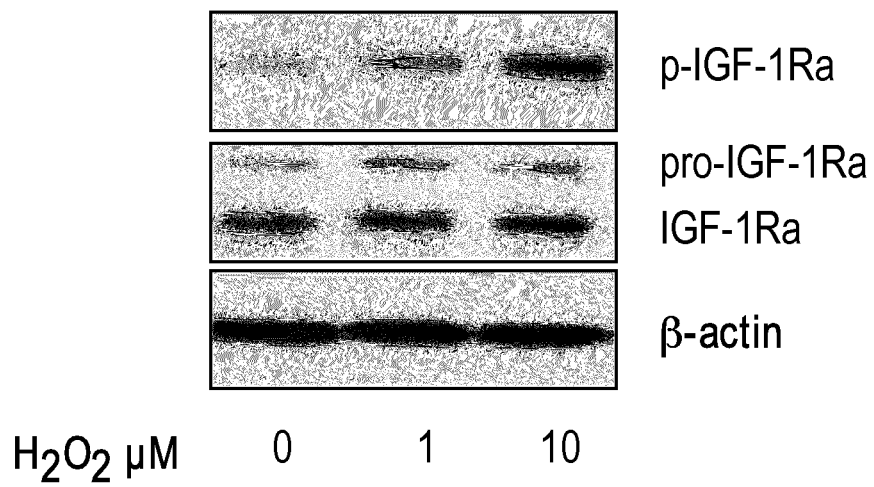
FIGS. 6A-C. $H_2O_2$ induces phosphorylation of IGF-1R. Subconfluent HPAEC were treated with 1 uM and 10 uM $H_2O_2$ and incubated in a $CO_2$ incubator. After 20 minutes, whole cell lysates were prepared and western blotting was performed to determine the phosphorylation status of IGF-1R, as shown in FIG. 6A. HPAEC were treated with 5 uM AG1024 for 30 minutes and then with 10 uM $H_2O_2$ for 20 minutes. Western blotting was then performed to determine phosphorylation status of IGF-1R, as shown in FIG. 6B. HPAEC were treated with 20 mM NAC and subjected to 10 Gy X-rays. Western blotting was then performed 3 hours post-irradiation to determine phosphorylation status of IGF-1R, as shown in FIG. 6C.
Figure 6B:
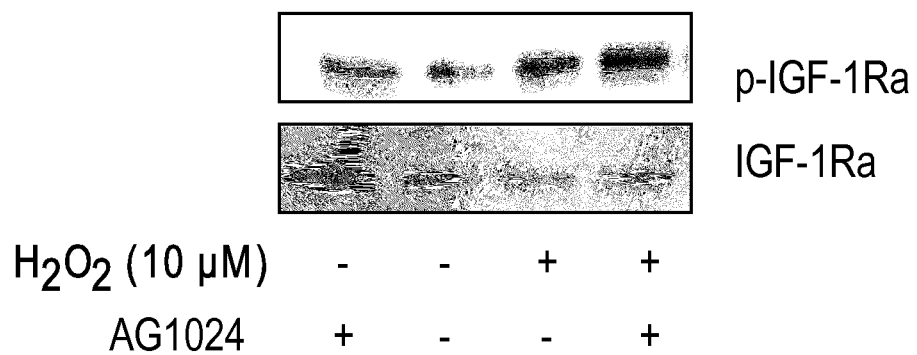
Figure 6C:
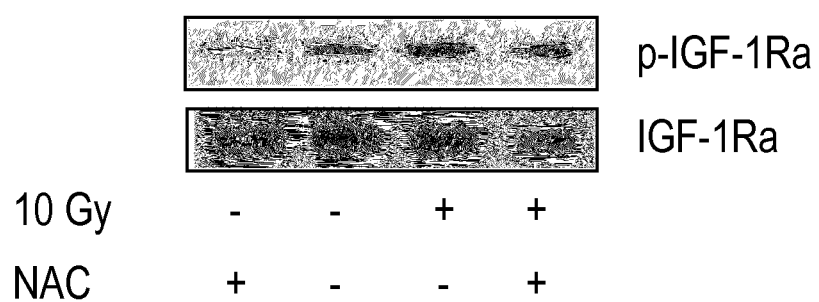

Radiation-induced reactive oxygen species (ROS) are required for early IGF-1R phosphorylation. Our data indicated that IGF-1R phosphorylation could be detected at time points that preceded the increased production of IGF ligands. We therefore investigated alternative mechanism of early IGF-1R activation. Exposure to IR is known to cause accumulation of ROS via radiolysis of intracellular $H_2O$ and through subsequent production of intracellular ROS (Leach, Van Tuyle et al. 2001; Hall and Giaccia 2006). ROS have also been shown to cause phosphorylation of cellular receptors, including IGF-1R in vascular smooth muscle cells (Bouallegue, Pandey et al. 2009; Weitsman, Weebadda et al. 2009). To determine whether ROS alone would be sufficient for the induction of IGF-1R phosphorylation, we treated HPAEC with $H_2O_2$ (1 μM and 10 μM) for 20 minutes. As shown in FIG. 6A, $H_2O_2$ alone was sufficient to induce IGF-1R phosphorylation. We then determined whether this ROS-induced phosphorylation is ligand-dependent by treating the cells with $H_2O_2$ in the presence of AG1024 and blotting for phosphorylated IGF-1R. As shown in FIG. 6B, ROS-induced IGF-1R phosphorylation is not inhibited by AG1024. Finally, to determine whether IR-induced IGF-1R phosphorylation is mediated by ROS, we treated HPAEC with 20 mM N-acetyl-L-cysteine (NAC) for 1 hour and exposed the cells to 10 Gy X-rays. Western blotting shows that IGF-1R phosphorylation was attenuated in the presence of NAC (FIG. 6C).

Figure 7A:
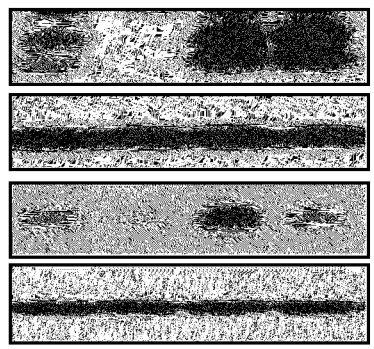
FIGS. 7A-B. Treatment with AG1024 or addition of IGF-1 does not regulate IR-induced apoptosis. (A) Subconfluent HPAEC were treated with 5 uM AG1024 or DMSO for 30 minutes and subjected to 50 Gy X-rays. At 6 hours post-irradiation, whole cell lysates were prepared and western blotting for cleaved, caspase-3 was performed, as shown in FIG. 7A. Subconfluent cultures of HPAEC were added with 10×IGF-1 concentration (50 ng/ml) for 18 hours and exposed to 10 Gy X-rays. At 6 hours post-irradiation, whole cell lysates were prepared and western blotting for cleaved, caspase-3 was performed, as shown in FIG. 7B.
Figure 7B:
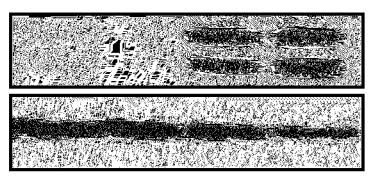

Treatment with AG1024 or increasing the concentration of IGF-1 has no effect on radiation-induced caspase-3 activation. A number of studies have shown that bypassing or blocking cellular senescence sensitizes cells to apoptosis following cellular stress (Rebbaa, Zheng et al. 2003; Drullion, Tregoat et al. 2012). In order to determine whether IGF-1R may play a role in this dynamic, we treated HPAEC with AG1024 (IGF-1R inhibitor) and exogenous IGF-1 (IGF-1R activator) and then exposed to the cells X-rays. For this purpose, we used 50 Gy X-rays as this is the dose we previously found to be effective in detecting caspase-3 activation in bovine PAEC (Panganiban, Mungunsukh et al. 2012). As shown in FIG. 7, treatment with either AG1024 or exogenous IGF-1 did not alter the levels of active caspase-3 suggesting that IGF-1R does not regulate radiation-induced apoptosis.

Figure 8A:
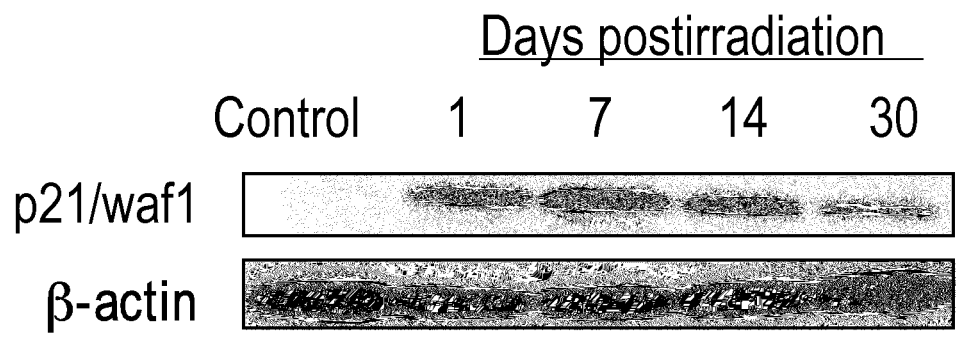
FIGS. 8A-C. X-rays induce cellular senescence in murine lung and skin tissue in a model of multi-organ injury. C57BL/6 mice were exposed to 17 Gy thoracic X-ray irradiation.
Figure 8B:
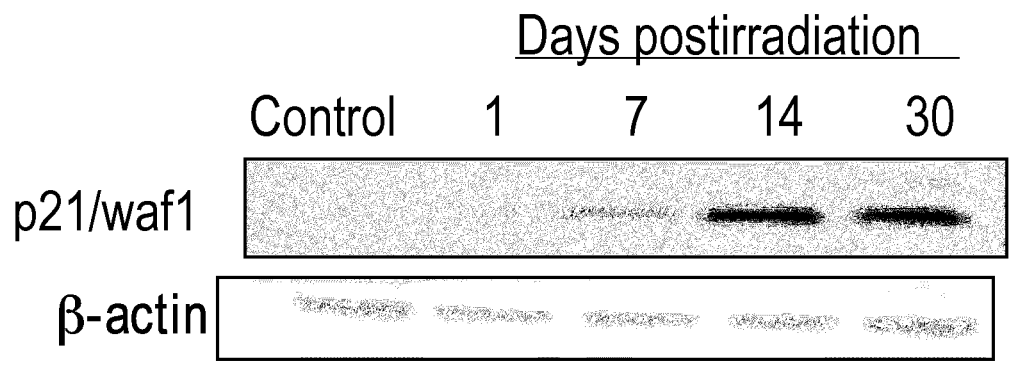
Figure 8C:
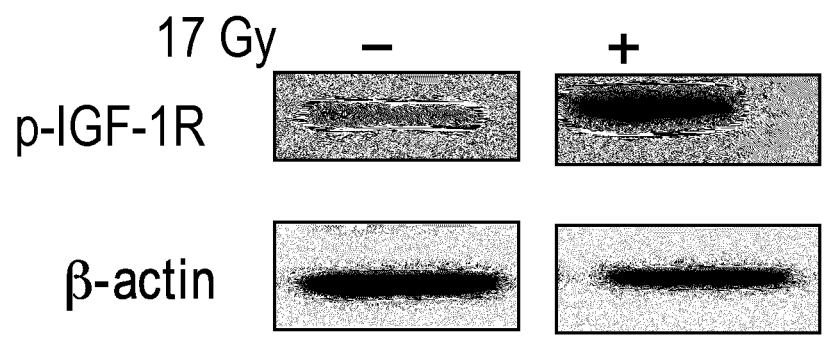

Radiation induced cellular senescence in vivo. 17 Gy thoracic irradiation induces pulmonary fibrosis in CBA and C57BL/6 mice. We investigated the induction of cellular senescence in the lung tissue from a murine model of radiation-induced tissue injuries. C57BL/6 mice were exposed to 17 Gy thoracic irradiation (0.6 Gy/min) Lung tissue was obtained from the mice at 1, 7, 14, and 30 days post-irradiation and used for western blotting for p21/waf. Blots were stripped and reprobed for β-actin as a loading control. p21/waf is upregulated in the lung within 1 day in response to 17 Gy thoracic irradiation (FIGS. 8A and 8B). In a similar manner, lung tissue was obtained 12-24 hours post-irradiation and used for western blotting for phosphorylated IGF-1R. Blots were stripped and reprobed for β-actin as a loading control. Phosphorylation of the IGF-1R in the lung increased within 24 hours post-irradiation (FIG. 8C).

Figure 10A:
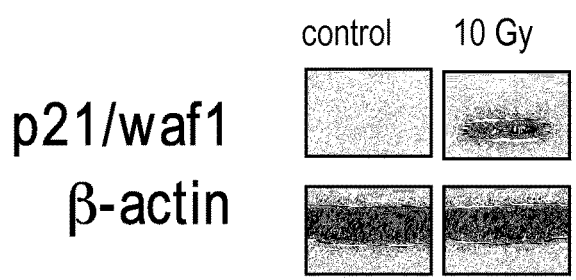
FIGS. 10A-B. Radiation induces accelerated senescence in primary human keratinocytes. Human keratinocytes were exposed to 10 Gy X-ray irradiation.
Figure 10B:
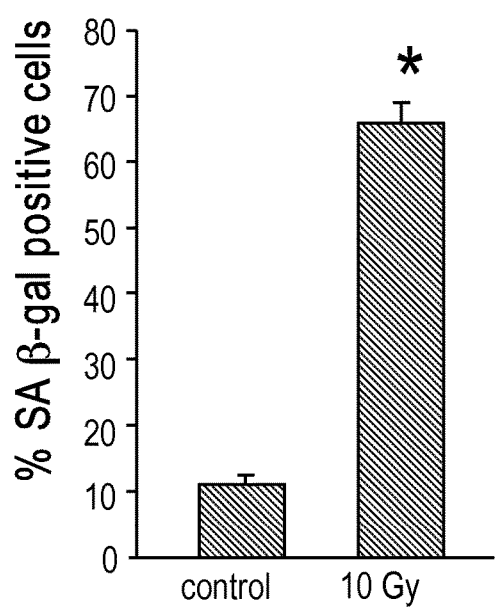

We also investigated the effects of radiation in primary human keratinocyte cultures. Human keratinocytes were exposed to 10 Gy X-ray irradiation. At 24 hours post-irradiation, cell lysates were prepared and blotted for p21/waf. Blots were stripped and probed for β-actin as a loading control. Samples were run on the same gel, but interviening lanes were removed. At 72 hours post-irradiation, cells were assayed for the expression of SA-β-gal. Consistent with our findings of accelerated cellular senescence in endothelial cells, we found that x-ray irradiation resulted in the upregulation of p21/waf and SA-β-gal in human keratinocytes (FIG. 10A). Up to about 70% of the keratinocyte population underwent senescence within 72 hours (FIG. 10B).

Discussion

Exposure to various stresses, especially to DNA damaging agents, triggers complex cellular responses that result in either cell survival or cell death. In most cases, cellular stresses may also induce cells to undergo accelerated senescence, a form of irreversible cell cycle arrest with complex phenotypes that includes extensive morphological alterations, secretion of senescence-associated proteins, and an increase in SA-β-gal activity (Muller 2009). We previously demonstrated that accelerated senescence is the primary mechanism of radiation-induced loss of clonogenicity in non-immortalized, non-cancer endothelial cells (Panganiban, Mungunsukh et al. 2012). In the current study, we provide evidence that IGF-1R activation is required for radiation-induced accelerated senescence, as inhibition of IGF-1R suppresses downstream activation of p53 and p21/waf1. Cells treated with the IGF-1R inhibitor maintain normal morphology and do not express SA-β-gal in response to x-ray irradiation. This is the first demonstration of the requirement of IGF-1R for accelerated senescence by ionizing radiation.

An accumulating body of evidence suggests that cellular senescence is a state of continuous cell growth signaling in the presence of a cell cycle blockade (Blagosklonny 2011). In support of this idea, mTOR has recently been suggested as the critical effector of the continuous cell growth response component of cellular senescence. Consistent with recent findings on the effects of blocking mTOR activity on the development of cellular senescence, our results suggest that radiation-induced cellular senescence involves mTOR as shown by attenuation of SA-β-gal activity in the presence of rapamycin. Interestingly, we also find that inhibition of mTOR results in attenuation of radiation-induced p21/waf1 expression suggesting that mTOR is possibly upstream of p21/waf1 in HPAEC following radiation exposure. Indeed, a number of studies have demonstrated crosstalk between p53/p21/waf1 and mTOR pathways via regulation of mouse double minute 2 homolog (MDM2) and and sirtuin 1 (SIRT1), which both modulate p53 accumulation (Lee, Inoki et al. 2007; Kojima, Shimanuki et al. 2008; Tran and University 2008).

Our current findings in HPAEC indicate that IGF-1R activation does not inhibit radiation-induced apoptosis. Paradoxically, a number of studies have demonstrated positive effects of activated IGF-1R and IGF-1 in conferring radiation resistance mostly through prevention of apoptosis in cancer cells. For example, increased IGF-1R phosphorylation after γ-irradiation was demonstrated even in the absence of detectable IGF-1 or IGF-1 ligands, triggering anti-apoptotic activity in non-small cell lung cancer cell line (Cosaceanu, Budiu et al. 2007). However, in other tumor cell types IGF-1R is dispensable for the induction of radiation resistance, suggesting that IGF-1R is anti-apoptotic in specific cell types and that the underlying mechanism(s) of radiation resistance in other cancer cells remain unresolved (Tezuka, M. et al. 2001). Our finding of the requirement of IGF-1R for radiation-induced accelerated senescence in primary endothelial cells and keratinocytes is consistent with the findings of a previous study on the requirement of functional IGF-1R for the initiation of UVB-induced premature senescence in primary human keratinocytes (Qiu, Leibowitz et al. 2010). However other IGF-1R-independent signaling mechanism(s) are likely activated for radiation-induced apoptosis in primary endothelial cells and keratinocytes.

The generation of ROS by ionizing radiation is the primary toxic stress that causes cellular macromolecular damage (Leach, Van Tuyle et al. 2001). Inhibition of the catalytic activity of phosphatases by ROS, especially protein tyrosine phosphatases, has been proposed as a mechanism for activation of kinases (Yu, Fuchshofer et al. 2009). ROS were demonstrated to induce the phosphorylation of IGF-1R in transformed cells, although it has not been determined whether this activation is direct or indirect through phosphatase inactivation (Lewis, Yi et al. 2008).

In agreement with these results, our data indicate that in primary HPAEC, ROS can also mediate IGF-1R activation. Our data indicate that the antioxidant NAC attenuated early IGF-1R phosphorylation induced by radiation. Together these findings imply the contribution of an ROS-dependent, ligand-independent mechanism for early activation of IGF-1R. However, our findings also indicate that a ligand-dependent mechanism likewise contributes to delayed IGF-1R activation following radiation exposure, as revealed by the increase in both IGF-1 mRNA and secreted protein. The increase in IGF-1 levels along with upregulation of IGF-2 for IGF-1R activation may contribute to a cycle of autocrine and paracrine signaling, which in HPAEC has been demonstrated to induce cell proliferation. In the presence of the cell cycle inhibitor p21/wafl this signaling may ultimately lead to the development of the complex senescent phenotype.

The importance of accelerated senescence in radiation-induced damage is being increasingly recognized with the discovery that mTOR mediates radiation-induced cellular senescence during exposure to radiation in vivo (Iglesias-Bartolome, Patel et al. 2012). Yet, the mechanisms of radiation-induced cellular senescence remain incompletely understood. Although senescent cells are metabolically active, they are incapable of replication and have altered cellular activities (Hampel, Malisan et al. 2004; Gosselin, Deruy et al. 2009). Importantly, radiation-induced cellular senescence may deplete the pool of proliferative cells, thus contributing to tissue repair failure following radiation exposure (Cosaceanu, Budiu et al. 2007). Here, we have provided evidence that IGF-1R signaling contributes to radiation-induced cellular senescence which can be blocked by pharmacological inhibitors. The identification of specific pathways and mechanisms for radiation-induced cellular senescence could provide novel targets for the prevention of the adverse effects of clinical radiation treatments or from accidental radiation exposures.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

Abboud, S. L., C. R. Bethel, et al. (1991). "*Secretion of insulin like growth factor I and insulinlike growth factor-binding proteins by murine bone marrow stromal cells.*" J Clin Invest 88(2): 470-475.

Anisimov, V. N., M. A. Zabezhinski, et al. (2011). "*Rapamycin increases lifespan and inhibits spontaneous tumorigenesis in inbred female mice.*" Cell Cycle 10(24): 4230-4236.

Astle, M. V., K. M. Hannan, et al. (2012). "*AKT induces senescence in human cells via mTORC1 and p53 in the absence of DNA damage: implications for targeting mTOR during malignancy.*" Oncogene 31(15): 1949-1962.

Bandyopadhyay, D., C. Gatza, et al. (2005). "*Analysis of cellular senescence in culture in vivo: the senescence-associated beta-galactosidase assay.*" Curr Protoc Cell Biol Chapter 18: Unit 18 19.

Baserga R (1999) *The IGF-I receptor in cancer research.* Exp Cell Res 253: 1-6.

Besancenot, R., R. Chaligne, et al. (2010). "*A senescence-like cell-cycle arrest occurs during megakaryocytic maturation: implications for physiological and pathological megakaryocytic proliferation.*" PLoS Biol 8(9).

Blagosklonny, M. V. (2011). "*Cell cycle arrest is not senescence.*" Aging (Albany N.Y.) 3(2): 94-101.

Blagosklonny, M. V. (2011). "*Progeria, rapamycin and normal aging: recent breakthrough.*" Aging (Albany N.Y.) 3(7): 685-691.

Bouallegue, A., N R. Pandey, et al. (2009). "*CaMKII knockdown attenuates H2O2-induced phosphorylation of ERK1/2, PKB/Akt, and IGF-1R in vascular smooth muscle cells.*" Free Radic Biol Med 47(6): 858-866.

Boucher, M. J., D. Jean, et al. (2004). "*Dual role of MEK/ERK signaling in senescence and transformation of intestinal epithelial cells.*" Am J Physiol Gastrointest Liver Physiol 286(5): G736-746.

Campisi, J. (2005). "*Senescent cells, tumor suppression, and organismal aging: good citizens, bad neighbors.*" Cell 120(4): 513-522.

Chenal, J., K Pierre, et al. (2008). "*Insulin and IGF-1 enhance the expression of the neuronal monocarboxylate transporter MCT2 by translational activation via stimulation of the phosphoinositide 3-kinase-Akt-mammalian target of rapamycin pathway.*" Eur J Neurosci 27(1): 53-65.

Clemmons, D. R. (2009). "*Role of IGF-1 in skeletal muscle mass maintenance.*" Trends Endocrinol Metab 20(7): 349-356.

Cosaceanu, D., R. A. Budiu, et al. (2007). "*Ionizing radiation activates IGF-1R triggering a cytoprotective signaling by interfering with Ku-DNA binding and by modulating Ku86 expression via a p38 kinase-dependent mechanism.*" Oncogene 26(17): 2423-2434.

Costantini, C., E. Lorenzetto, et al. (2010). "*Astrocytes regulate the expression of insulin-like growth factor 1* receptor (IGF 1-R) in primary cortical neurons during in vitro senescence." J Mol Neurosci 40(3): 342-352.

Demidenko, Z. N and M. V. Blagosklonny (2008). "Growth stimulation leads to cellular senescence when the cell cycle is blocked." Cell Cycle 7(21): 3355-3361.

Dimri, G. P., X Lee, et al. (1995). "A biomarker that identifies senescent human cells in culture and in aging skin in vivo." Proc Natl Acad Sci USA 92(20): 9363-9367.

Dricu, A., M. Carlberg, et al. (1997). "Inhibition of N-linked glycosylation using tunicamycin causes cell death in malignant cells: role of down-regulation of the insulin-like growth factor 1 receptor in induction of apoptosis." Cancer Res 57(3): 543-548.

Dricu, A., M. Wang, et al. (1997). "Mevalonate-regulated mechanisms in cell growth control: role of dolichyl phosphate in expression of the insulin-like growth factor-1 receptor (IGF-1R) in comparison to Ras prenylation and expression of c-myc." Glycobiology 7(5): 625-633.

Drullion, C., C. Tregoat, et al. (2012). "Apoptosis and autophagy have opposite roles on imatinib-induced K562 leukemia cell senescence." Cell Death Dis 3: e373.

Ferrari S, Bandi HR, Hofsteenge J. Bussian BM, Thomas G (1991) Mitogen-activated 70K S6 kinase. Identification of in vitro 40 S ribosomal S6 phosphorylation sites. J Biol Chem 266: 22770-22775.

Floratou, K., E. Giannopoulou, et al. (2012). "Oxidative stress due to radiation in CD34+ Hematopoietic progenitor cells: protection by IGF-1." J Radiat Res 53(5): 672-685.

Freund, A., R. M. Laberge, et al. (2012). "Lamin B1 loss is a senescence-associated biomarker." Mol Biol Cell 23(11): 2066-2075.

Gosselin, K., E. Deruy, et al. (2009). "Senescent keratinocytes die by autophagic programmed cell death." Am J Pathol 174(2): 423-435.

Hall, E. J. and A. J. Giaccia (2006). Radiobiology for the radiologist. Philadelphia, Lippincott Williams & Wilkins.

Hampel, B., F. Malisan, et al. (2004). "Differential regulation of apoptotic cell death in senescent human cells." Exp Gerontol 39(11-12): 1713-1721.

Handayaningsih, A. E., M. Takahashi, et al. (2012). "IGF-I enhances cellular senescence via the reactive oxygen species-p53 pathway." Biochem Biophys Res Commun 425(2): 478-484.

Holzenberger, M., J. Dupont, et al. (2003). "IGF-1 receptor regulates lifespan and resistance to oxidative stress in mice." Nature 421(6919): 182-187.

Iglesias-Bartolome, R., V. Patel, et al. (2012). "mTOR inhibition prevents epithelial stem cell senescence and protects from radiation-induced mucositis." Cell Stem Cell 11(3): 401-414.

Jeyapalan, J. C., M. Ferreira, et al. (2007). "Accumulation of senescent cells in mitotic tissue of aging primates." Mech Ageing Dev 128(1): 36-44.

Khalid, M., W. Haresign, et al. (2000). "Secretion of IGF-1 by ovine granulosa cells: effects of growth hormone and follicle stimulating hormone." Anim Reprod Sci 58(3-4): 261-272.

Kojima, K, M. Shimanuki, et al. (2008). "The dual PI3 kinase/mTOR inhibitor PI-103 prevents p53 induction by Mdm2 inhibition but enhances p53-mediated mitochondrial apoptosis in p53 wild-type AML." Leukemia 22(9): 1728-1736.

Laplante, M and D. M Sabatini (2012). "mTOR signaling in growth control and disease." Cell 149(2): 274-293.

Leach, J. K, G. Van Tuyle, et al. (2001). "Ionizing radiation-induced, mitochondria-dependent generation of reactive oxygen/nitrogen." Cancer Res 61(10): 3894-3901.

Lee, C. H., K Inoki, et al. (2007). "Constitutive mTOR activation in TSC mutants sensitizes cells to energy starvation and genomic damage via p53. " EMBO J 26(23): 4812-4823.

Leontieva, 0. V. and M V. Blagosklonny (2010). "DNA damaging agents and p53 do not cause senescence in quiescent cells, while consecutive re-activation of mTOR is associated with conversion to senescence." Aging (Albany N.Y.) 2(12): 924-935.

Leontieva, O. V., Z. N Demidenko, et al. (2011). "Elimination of proliferating cells unmasks the shift from senescence to quiescence caused by rapamycin." PLoS One 6(10): e26126.

Leontieva, O. V., A. V. Gudkov, et al. (2010). "Weak p53 permits senescence during cell cycle arrest." Cell Cycle 9(21): 4323-4327.

LeRoith, D., R. Baserga, et al. (1995). "Insulin-like growth factors and cancer." Ann Intern Med 122(1): 54-59.

LeRoith, D., S. Neuenschwander, et al. (1995). "Insulin-like growth factor-I and insulin-like growth factor binding protein-3 inhibit involution of the mammary gland following lactation: studies in transgenic mice." Prog Growth Factor Res 6(2-4): 433-436.

Lewis, D. A., Q. Yi, et al. (2008). "UVB-induced senescence in human keratinocytes requires a functional insulin-like growth factor-1 receptor and p53." Mol Biol Cell 19(4): 1346-1353.

Lopaczynski W, Terry C, Nissley P (2000) Autophosphorylation of the insulin-like growth factor I receptor cytoplasmic domain. Biochem Biophys Res Commun 279: 955-960.

Miyauchi, H., T Minamino, et al. (2004). "Akt negatively regulates the in vitro lifespan of human endothelial cells via a p53/p21-dependent pathway." EMBO J 23(1): 212-220.

Muller, M. (2009). "Cellular senescence: molecular mechanisms, in vivo significance, and redox considerations." Antioxid Redox Signal 11(1): 59-98.

Nogueira, V., Y. Park, et al. (2008). "Akt determines replicative senescence and oxidative or oncogenic premature senescence and sensitizes cells to oxidative apoptosis." Cancer Cell 14(6): 458-470.

Oldham, S. and E. Hafen (2003). "Insulin/IGF and target of rapamycin signaling: a TOR de force in growth control." Trends Cell Biol 13(2): 79-85.

Panganiban, R. A., O. Mungunsukh, et al. (2012). "X-irradiation induces ER stress, apoptosis, and senescence in pulmonary artery endothelial cells." Int J Radiat Biol.

Persad S, Attwell S, Gray V, Mawji N, Deng J T, et al. (2001) Regulation of protein kinase B/Akt-serine 473 phosphorylation by integrin-linked kinase: critical roles for kinase activity and amino acids arginine 211 and serine 343. J Biol Chem 276: 27462-27469.

Qiu, W, B. Leibowitz, et al. (2010). "Growth factors protect intestinal stem cells from radiation-induced apoptosis by suppressing PUMA through the PI3K/AKT/p53 axis." Oncogene 29(11): 1622-1632.

Rebbaa, A., X Zheng, et al. (2003). "*Caspase inhibition switches doxorubicin-induced apoptosis to senescence.*" Oncogene 22(18): 2805-2811.

Riedemann, J and V. M. Macaulay (2006). "*IGF1R signalling and its inhibition.*" Endocr Relat Cancer 13 Suppl1: S33-43.

Rios-Moreno, M. J., S. Jaramillo, et al. (2011). "*Differential activation of MAPK and PI3K/AKT/mTOR pathways and IGF1R expression in gastrointestinal stromal tumors.*" Anticancer Res 31(9): 3019-3025.

Salatino, M., R. Schillaci, et al. (2004). "*Inhibition of in vivo breast cancer growth by antisense oligodeoxynucleotides to type I insulin-like growth factor receptor mRNA involves inactivation of ErbBs, PI-3K/Akt and p42/p44 MAPK signaling pathways but not modulation of progesterone receptor activity.*" Oncogene 23(30): 5161-5174.

Tezuka, M., H. Watanabe, et al. (2001). "*Antiapoptotic activity is dispensable for insulin-like growth factor I receptor-mediated clonogenic radioresistance after gamma-irradiation.*" Clin Cancer Res 7(10): 3206-3214.

Tran, D. (2008). *IGF-1 induces premature cellular senescence through inhibition of Sirt1 and activation Ofp53, Boston University, Division of Graduate Medical Sciences Dissertation.*

Tran, D. and B. University (2008). *IGF-1 Induces Premature Cellular Senescence Through Inhibition of SirT1 and Activation Ofp53, Boston University.*

Turner, B. C., B. G. Haffty, et al. (1997). "*Insulin-like growth factor-I receptor overexpression mediates cellular radioresistance and local breast cancer recurrence after lumpectomy and radiation.*" Cancer Res 57(15): 3079-3083.

Valenciano, A., L. A. Henriquez-Hernandez, et al. (2012). "*Role of IGF-1 receptor in radiation response.*" Transl Oncol 5(1): 1-9.

Weitsman, G. E., W. Weebadda, et al. (2009). "*Reactive oxygen species induce phosphorylation of serine 118 and 167 on estrogen receptor alpha.*" Breast Cancer Res Treat 118(2): 269-279.

Werner, H., G. G. Re, et al. (1993). "*Increased expression of the insulin-like growth factor I receptor gene, IGF1R, in Wilms tumor is correlated with modulation of IGF 1R promoter activity by the WT1 Wilms tumor gene product.*" Proc Natl Acad Sci USA 90(12): 5828-5832.

Yu, A. L., R. Fuchshofer, et al. (2009). "*Subtoxic oxidative stress induces senescence in retinal pigment epithelial cells via TGF-beta release.*" Invest Ophthalmol Vis Sci 50(2): 926-9.

---

What is claimed:

1. A method of reducing cellular senescence in non-cancerous keratinocytes that have been exposed to ionizing radiation, the method comprising administering to a subject before, after, or concurrently with exposure to ionizing radiation a compound that inhibits activation of an insulin-like growth factor-1 receptor (IGF-1R) or a compound that inhibits a protein involved in an IGF-1R induced signaling cascade, wherein the compound is administered in an amount effective to reduce cellular senescence in non-cancerous keratinocytes in the subject, wherein the subject has skin cancer, and wherein the subject does not have prostate cancer.

2. The method of claim 1, wherein the compound that inhibits activation of the IGF-1R is an IGF-1R inhibitor.

3. The method of claim 1, wherein the compound that inhibits activation of the IGF-1R is an insulin growth factor-1 (IGF-1) inhibitor or an insulin growth factor-2 (IGF-2) inhibitor.

4. The method of claim 1, wherein the compound is an antibody.

5. The method of claim 4, wherein the antibody binds to IGF-1R.

6. The method of claim 2, wherein the IGF-1R inhibitor is BMS 754807;
   OSI-906; figitumumab (CP-751871); NT52; INSM-18; NVP-AEW541; NVP-ADW742; aIR3;
   IGF1R scFv-Fc; 486/STOP; 950/STOP; N-(2-methoxy-5-chlorophenyl)-N'-(2-methylquinolin-4-yl)- urea; BMS-754807; IGF-IRi; AG1024; R1507; AXL-1717; picropodophyllotoxin; PQ401;
   dalotuzumab; A-928605; KW-2450; BMS-536924; IMC-A12; CP-751871; n-(5-chloro-2-methoxyphenyl)-N'-(2-methoxyquinolin-4-yl)-urea; TAE226; BMS-554417; MK-0646; BMS-536924; MAE87; XL 228; AGL 2263; I-OMe-AG538; AG538; OSI-868; BMS-754807;
   ADW742; NVP-ADW642; R1507; MK-0646; A928605; MAB391; BMS-536942; IMC-A12;
   rhIGFBP3, ANT-429, ATL-1101, BVP-51004, JV-1-38, pegvisomant, A-928605, or PPP (CAS 477-47-4).

7. The method of claim 6, wherein the IGF-1R inhibitor is AG1024.

8. The method of claim 3, wherein the IGF-1 inhibitor is PPP (CAS 477-47-4).

9. The method of claim 1, wherein the compound that inhibits a protein involved in an IGF-1R induced signaling cascade is a PI3K inhibitor or an IRS-1 inhibitor.

10. The method of claim 9, wherein the PI3K inhibitor is Ly294002, Wortmannin, BEZ235 (NVP-BEZ235), GDC-0941, PI-103, BKM120 (NVP-BKM120), CAL-101 (GS-1101), IC-87114, GSK2636771, TG 100713, BYL719, PI3K/HDAC inhibitor 1, 3-Methyladenine, YM201636, NVP-BGT226, BAY80-6946, PF-04691502, PKI-402, CH5132799, GDC-0980 (RG7422), NU 7026, NU 7441 (KU-57788), AS-252424, AS-604850, AS-041164, CAY10505, GSK2126458, A66, PF-05212384 (PKI-587), PIK-294, PIK-293, XL765, PIK-93, AZD6482, AS-605240, GSK1059615, TG100-115, PIK-75, PIK-90, TGX-115, TGX-221, XL147, ZSTK474, quercetin, tetrodotoxin citrate, thioperamide maleate, PI103, (−)-deguelin, OSU03012, tandutinib, GSK690693, KU-55933, MK-2206, perifosine, triciribine, PI828, WHI-P 154, compound 15e, 17-P-hydroxywortmannin, Pp 121, PX-478, PX-866, PX-867, WAY-266176, WAY-266175 SF1126, 07-112, IC-486068, or LME00084.

11. The method of claim 10, wherein the PI3K inhibitor is LY-294002.

12. The method of claim 1, wherein IGF-1R or the compound that inhibits a protein involved in an IGF-1R induced signaling cascade is administered before, after, or concurrently with exposure to ionizing radiation to protect non-cancerous keratinocytes in the subject from radiation-induced cellular senescence.

13. The method of claim 1, where the compound that inhibits a protein involved in an IGF-1R induced signaling cascade is administered no more than 14, 7, 6, 5, 4, 3, 2, or 1 days before or after the subject is exposed to ionizing radiation.

14. The method of claim 12, wherein the compound that inhibits activation of an insulin-like growth factor receptor (IGF-1R) or the compound that inhibits a protein involved in an IGF-1R induced signaling cascade is administered concurrently with exposure to ionizing radiation.

15. The method of claim 1, wherein the subject is a mammal.

16. The method of claim 1, wherein the subject is a human.

17. A method of reducing cellular senescence in non-cancerous cells that have been exposed to ionizing radiation, the method comprising administering to a subject before, after, or concurrently with exposure to ionizing radiation a compound that inhibits activation of an insulin-like growth factor-1 receptor (IGF-1R) or a compound that inhibits a protein involved in an IGF-1R induced signaling cascade, wherein the compound is administered in an amount effective to reduce cellular senescence in non-cancerous cells in the subject, wherein the subject has been accidently exposed to ionizing radiation.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcctgtccc ctccttctgt t                                             21

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcccaagac ccagaagt                                                 18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acaccctcca gttcgtctgt                                               20

<210> SEQ ID NO 4
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 4
gaaacagcac tcctcaacga                                                    20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaagctcgtc atcaatggaa a                                                  21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccacttgatg ttggcaggat                                                    20
```